(12) United States Patent
Takagi

(10) Patent No.: US 8,035,817 B2
(45) Date of Patent: Oct. 11, 2011

(54) METHOD FOR ESTIMATING REFLECTANCE

(75) Inventor: Atsushi Takagi, Toyota (JP)

(73) Assignee: Toyota Jidosha Kabushiki Kaisha, Toyota-Shi, Aichi-Ken (JP)

( * ) Notice: Subject to any disclaimer, the term of this patent is extended or adjusted under 35 U.S.C. 154(b) by 395 days.

(21) Appl. No.: 12/373,942

(22) PCT Filed: Jul. 23, 2007

(86) PCT No.: PCT/JP2007/064415
§ 371 (c)(1),
(2), (4) Date: Jan. 15, 2009

(87) PCT Pub. No.: WO2008/010592
PCT Pub. Date: Jan. 24, 2008

(65) Prior Publication Data
US 2009/0316156 A1  Dec. 24, 2009

(30) Foreign Application Priority Data

Jul. 21, 2006 (JP) ................................. 2006-199967

(51) Int. Cl.
*G01N 21/55* (2006.01)
*G01N 21/47* (2006.01)
(52) U.S. Cl. ....................... 356/445; 356/446
(58) Field of Classification Search .......................... None
See application file for complete search history.

(56) References Cited

U.S. PATENT DOCUMENTS

| | | | |
|---|---|---|---|
| 4,572,672 A | 2/1986 | Orchard et al. | |
| 5,502,799 A | 3/1996 | Tsuji et al. | |
| 6,249,751 B1 | 6/2001 | Asaba et al. | |
| 2003/0193669 A1 | 10/2003 | Takagi | |
| 2006/0092412 A1 | 5/2006 | Doshoda et al. | |

FOREIGN PATENT DOCUMENTS

CN   1766577 A   5/2006
(Continued)

OTHER PUBLICATIONS

Takagi, A., et al., "Prediction of Spectral Reflectance Factor Distribution of Automotive Paint Finishes," Color Research and Application, vol. 30, No. 4, Aug. 2005, pp. 275-282.

(Continued)

*Primary Examiner* — Gregory J Toatley
*Assistant Examiner* — Amanda Merlino
(74) *Attorney, Agent, or Firm* — Finnegan, Henderson, Farabow, Garrett & Dunner, LLP

(57) ABSTRACT

A reflectance of a color shifted painting color is also measured conveniently.
A first reflectance $R(\alpha_a)$ of a first reflected light $V_a$ inside an incident plane A is measured, and a first locus l of termini of first bisection vectors $H_a$ ($|H_a|=|R(\alpha_a)|$), which displaces two-dimensionally inside the incident plane A, is determined. A second reflectance $R(\alpha_b)$ of a second reflected light $V_b$ outside the incident plane A is measured, and a second locus m of termini of second bisection vectors $H_b$ ($|H_b|=|R(\alpha_b)|$), which displaces three-dimensionally outside the incident plane A, is measured. A locus n (x, y, $z_i$) of a terminus of a bisection vector $H_i$ on a plane z=z that is parallel to a plane under measurement is approximately modeled with a numerical equation showing an ellipse from the first locus l and the second locus m, thereby determining an approximation model equation, and an overall locus n' (x, y, z) of the overall termini of bisection vectors H' of reflected lights V' other than the first reflected light $V_a$ and the second reflected light $V_b$ is approximately determined.

6 Claims, 7 Drawing Sheets

FOREIGN PATENT DOCUMENTS

| | | |
|---|---|---|
| EP | 0087222 A2 | 8/1983 |
| EP | 1 353 156 A2 | 10/2003 |
| JP | 58-148942 A | 9/1983 |
| JP | 5-322655 | 12/1993 |
| JP | 11-230831 | 8/1999 |
| JP | 2003-307456 | 10/2003 |
| JP | 2006-153846 | 6/2006 |
| WO | WO 2004/097383 | 11/2004 |

OTHER PUBLICATIONS

Takagi, A., "Prediction of Spectral Reflectance Factor Distribution of Color-Shift Paint Finishes," Color Research and Application, vol. 32, No. 5, Oct. 2007, pp. 378-387.

Li, H., et al., Automated three-axis gonioreflectometer for computer graphics applications, Proceedings of the SPIE—The International Society for Optical Engineering SPIE—The International Society for Optical Engineering USA, vol. 5878, 2005, pp. 58780S-1-69890S-11.

Jafolla, J., et al., "Phenomenological BRDF Modeling for Engineering Applications," Proceedings of the International Society for Optical Engineering, vol. 3141, Jan. 1, 1997, pp. 281-292.

Germer, T., et al., "Ray model of light scattering by flake pigments or rough surfaces with smooth transparent coatings," Applied Optics, vol. 43, No. 6, Feb. 20, 2004, pp. 1266-1274.

Extended European Search Report for EP Appl. No. 07791148.5, dated Nov. 18, 2010.

International Preliminary Report on Patentability, mailed Jan. 27, 2009, for PCT/JP2007/064415.

(a)

(b)

METHOD FOR ESTIMATING REFLECTANCE

CROSS-REFERENCE TO RELATED APPLICATIONS

This application is a national phase application of International Application No. PCT/JP2007/064415, filed Jul. 23, 2007, and claims the priority of Japanese Application No. 2006-199967, filed Jul. 21, 2006, the contents of both of which are incorporated herein by reference.

TECHNICAL FIELD

The present invention relates to a method for estimating a reflectance and, more particularly, to a method for estimating a reflectance, which is suited to the examining of reflection characteristics of a color shifted painting color.

BACKGROUND ART

Color and brightness of a painting color applied to a body of a motor vehicle depend on a viewing direction. Such appearance of the painting color can be expressed numerically with the reflection characteristics of a painted plane, namely the reflectance thereof. Therefore, by measuring the reflectance of the painting color, the quality thereof can be adjusted in the producing step and the testing step of the painting color, and the painting color can be examined using computer graphics (CG) prior to painting. Consequently, it is important to measure the reflectance of the painting color. And, it is an important problem how the measuring conditions of the reflectance of the painted plane are set.

It has been known that the reflection characteristics of a general painting color applied to a vehicle body can be sufficiently obtained by measuring the reflectance when light made incident at an incident angle of 60° is received at representative five displacement angles of about 10° (10°±several degree), about 18° (18°±several degree), about 28° (28°±several degree), about 40° (40°±several degree) and about 90° (90°±several degree) (see Patent Document 1, for example).

In this Patent Document 1, when the light made incident on an incident point P on a plane under measurement at an incident angle θ regularly reflects inside an incident plane A at a reflection angle θ, the regularly reflecting direction is expressed by a displacement angle of 0°, and the angle from the regularly reflecting direction toward a normal line at the incident point P on the pane under measurement (the side from the regularly reflecting direction toward the normal line is positive, whereas the side toward the plane under measurement opposite to the normal line is negative) is expressed by a displacement angle.

In this five angles method, reflectances of the light received at representative five displacement angles within a single incident plane are measured and interpolated. With this method, the reflectance of a complicated painting color such as a metallic color, pearl mica, etc. other than a solid color can be measured conveniently.

Patent Document 1: Patent application laid-open No. 2003-307456

DISCLOSURE OF THE INVENTION

Problem to be Solved with the Invention

In recent years, in order to meet the diversification and differentiation of market needs in the automobile trade, color shifted painting color (special painting color) such as maziora (Nippon Paint Co., Ltd.) has been developed and gradually used in market. Therefore, there has been required the measuring method of the reflectance, by which the reflection characteristics of the color shifted painting color can be quantified.

The color shifted painting color, however, has the characteristics that it is seen remarkably differently as the position of the light source varies. Consequently, with respect to the reflected light of the color shifted painting color, the directions outside the incident plane are also required to be considered. Therefore, with the above-described conventional five angles method of receiving light at the representative five displacement angles inside a single incident plane, the reflectance of the color shifted painting color has not been able to be measured accurately.

Hereinafter, the fact that the reflectance of the color shifted painting color cannot be measured accurately with the above-described conventional five angles method will be explained more specifically.

The conventional five angles method measures the reflectance at a time when light is received at the representative five angles inside a single incident plane, and premises that the painting color to be measured satisfies the following two conditions (a) and (b).

(a) The displacement angle characteristics do not vary when the incident angle varies (there is no incident angle dependence).

(b) The displacement angle characteristics do not vary irrespective of whether the displacement angle is positive or negative (the displacement angle characteristics exhibit symmetric properties at the displacement angle of 0°).

However, it has become clear based on the following studies and researches by the present inventor that the color shifted painting color does not satisfy the above-described two conditions, and consequently, the above-described conventional five angles method cannot be used for the color shifted painting color.

The present inventor has studied and researched in characteristics of color shifted painting color from the view points whether there is the incident angle dependence or not and whether there is the symmetric properties in displacement angle characteristics at the displacement angle of 0°, and, hereinafter, the results will be shown.

In the following results of the studies and researches, light is made incident on a single incident plane at an incident angle of θ, and a painting color at the displacement angle α inside the incident plane is expressed by an L*a*b* value, and represented by $c(\theta, \alpha) = (L^*_\theta(\alpha), a^*_\theta(\alpha), b^*_\theta(\alpha))$.

(Incident Angle Dependence)

With respect to 194 kinds of sample painting colors inclusive of a certain color shifted painting color (773 (emerald SS) manufactured by Nippon Paint Co., Ltd.), $c(60, \alpha)$, $c(45, \alpha)$ and $c(50, \alpha)$ at the incident angle θ of 60°, 45° and 50°, were respectively obtained.

And, with respect to various sample painting colors, an average value of a color difference in each displacement angle between the case of the incident angle θ being 60° and the case of the incident angle θ being 45° (an average color difference between 60° and 45°) was defined as shown in the following equation (1) and obtained.

Similarly, with respect to various sample painting colors, an average value of a color difference in each displacement angle between the case of the incident angle θ being 60° and the case of the incident angle θ being 50° (an average color difference between 60° and 50°) was defined as shown in the following equation (2) and obtained.

If there is no incident angle dependence, the average color difference between 60° and 45°, which is defined by the following equation (1), and the average color difference between 60° and 50°, which is defined by the above-described equation (2), must be 0, respectively.

And, since the measurement data at a time when light is received in the vicinity of a regularly reflecting direction includes measurement errors, the measurement data of $0 \leq \alpha \leq 9$ was eliminated.

$$\Delta \overline{E}_{60-45} = \frac{1}{81} \sum_{\alpha=10}^{90} \|c(60, \alpha) - c(45, \alpha)\| \quad (1)$$

$$\Delta \overline{E}_{60-50} = \frac{1}{81} \sum_{\alpha=10}^{90} \|c(60, \alpha) - c(50, \alpha)\| \quad (2)$$

As a result, in the case of a general painting color satisfying the above described two conditions (a) and (b), the average color difference between 60° and 45° became 3.50, whereas the average color difference between 60° and 50° became 2.53. It has become clear from these results that in the general painting color, the displacement angle characteristics scarcely vary, and that there is scarcely exhibited any incident angle dependence when the incident angle varies from 60° to 45°, or when the incident angle varies from 60° to 50°.

In contrast, in the case of the color shifted painting color, the average color difference between 60° and 45° became 15.60, whereas the average color difference between 60° and 50° became 11.55. It has become clear from these results that in the color shifted painting color, the displacement angle characteristics vary with the variation of the incident angle, and there is exhibited the incident angle dependence.

(Symmetric Properties of Displacement Angle Characteristics at Displacement Angle 0°)

Next, with respect to each of the sample painting colors, the displacement angle α on the side of a light source was varied between 10 and 20° at an incident angle of 60°, while varying the displacement angle –α on the side of a plane under measurement between –10 and –20°, and an average value of a color difference between positive and negative of displacement angle was obtained by the following equation (3).

In this case, if there are symmetric properties in the displacement angle characteristics at the displacement angle of 0°, the average color difference between positive and negative of the displacement angle, which is defined by the following equation (3), must be 0.

$$\Delta \overline{E}_{60} = \frac{1}{11} \sum_{\alpha=10}^{20} \|c(60, \alpha) - c(60, -\alpha)\| \quad (3)$$

And with respect to each of the sample painting colors, at the incident angles of 45° and 50°, the average color difference between positive and negative of the displacement angle was examined, similarly.

As a result, in the case of the general painting color satisfying the above-described two conditions (a) and (b), the average color difference between positive and negative of the displacement angle was 7.30 at the incident angle of 45°, 7.00 at the incident angle of 50°, and 6.96 at the incident angle of 60°. These results show that in the case of the general painting color, the displacement angle characteristics do not vary greatly at any incident angle, irrespective of whether the displacement angle is positive or negative, and that there was almost symmetric properties in the displacement angle characteristics at the displacement angle of 0°.

In contrast, in the case of the color shifted painting color, the average color difference between positive and negative of the displacement angle was 33.66 at the incident angle of 45°, 54.18 at the incident angle of 50°, and 65.79 at the incident angle of 60°. These results show that in the case of the color shifted painting color, the displacement angle characteristics greatly vary at any incident angle according to the positive or negative of the displacement angle, and that there were no symmetric properties in the displacement angle characteristics at the displacement angle of 0°.

These studies and researches show that the color shifted painting color do not satisfy the above-described two conditions (a) and (b), and consequently, the above-described conventional five angles method of measuring the reflectance by varying the representative five displacement angles only inside the single incident plane on the premise of the above-described two conditions (a) and (b), cannot be used for the color shifted painting color.

Namely, in the case of the color shifted painting color, it has become clear that the reflecting lights reflecting in the directions excluded in the incident plane must be considered, and accordingly, in principle, the reflectance is needed to measure at all points with respect to all incident and refection angles, unless a novel measuring method is used.

However, in the all points measuring method, the measuring points become too many, and a too long measuring time is needed so that this method is not practical. If the reflectance is measured at every 4° of the incident angle, at every 2° of the reflection angle, at every 4° of the azimuth angle, while varying the incident angle from 0 to 90°, the reflection angle from –90 to 90°, and the azimuth angle (angle between an incident plane and a reflection plane) from 0 to 90°, the measurement is needed at 48139(=23×91×23) points in total. In order to perform the measurement at each point, normally, about 9 to 10 seconds are required, and consequently, in order to perform the measurement at 48139 points, a too long measuring period of time as long as about 16 days is required provided that 8 hours per day are used for measurement.

Thus, under the present circumstances, convenient measuring methods of the reflectance of the color shifted painting color have not been established.

The present invention has been made in view of the above-described circumstances, and to solve a technical problem of measuring the reflectance of the color shifted painting color conveniently.

Means for Solving the Problems

In order to reduce the measuring period of time upon measuring the reflectance of a color shifted painting color, the present inventor has contemplated decreasing of the measurement points using two methods: reciprocity in reflectance of a painting color, and modeling of a reflected light distribution, and have confirmed that these methods are effective from their studies and researches, thereby completing the present invention.

Namely, the method for estimating a reflectance in accordance with the present invention is the method for estimating a reflectance at an arbitrary displacement angle inside an incident plane A and outside the incident plane A, upon taking an angle between a regularly reflected light S of an incident light L, which is regularly reflected inside the incident plane A when the incident light L is made incident on an incident point P on a plane under measurement at a predetermined incident angle θ, and a reflected light V of the incident light L, which is reflected and received from the incident point P, as a displacement angle α, and is provided with a first reflectance measuring step, a first locus determining step, a second reflectance measuring step, a second locus determining step, a two intersections coordinate determining step, a model equation determining step and an overall locus determining step.

In the first reflectance measuring step, upon making an incident light $L_d$ incident on the incident point P inside the incident plane A at an incident angle $\theta_d$, and receiving light at predetermined displacement angles $\alpha_1, \alpha_2, \ldots$ inside the incident plane A, first reflectances $R(\alpha_{a1}), R(\alpha_{a2}), \ldots$ of first reflected lights $V_{a1}, V_{a2}, \ldots$ inside the incident plane A relative to the incident light $L_d$ are measured.

In the first locus determining step, by taking bisection vectors between the incident light $L_d$ and each of the first reflected lights $V_{a1}, V_{a2}, \ldots$ as first bisection vectors $H_{a1}, H_{a2}, \ldots$, and defining the magnitude of the first reflectance $R(\alpha_a)$ is as $|H_a|=|R(\alpha_a)|$, a first locus l of termini of the first bisection vectors $H_{a1}, H_{a2}, \ldots$ as a curve displacing two-dimensionally inside the incident plane A is determined from the measurement results of the first reflectances $R(\alpha_{a1}), R(\alpha_{a2}), \ldots$.

In the second reflectance measuring step, upon making an incident light $L_d$ incident on the incident point P inside the incident plane A at the incident angle $\theta_d$ and receiving light at predetermined displacement angles $\alpha_1, \alpha_2, \ldots$ outside the incident plane A, second reflectances $R(\alpha_{b1}), R(\alpha_{b2}), \ldots$ of second reflected lights $V_{b1}, V_{b2}, \ldots$ outside the incident plane A relative to the incident light $L_d$ are measured.

In the second locus determining step, by taking bisection vectors between the incident light $L_d$ and each of the second reflected lights $V_{b1}, V_{b2}, \ldots$ as second bisection vectors $H_{b1}, H_{b2}, \ldots$, and defining the magnitude of the second reflectance $R(\alpha_b)$ as $|H_b|=|R(\alpha_b)|$, a second locus m of termini of the second bisection vectors $H_{b1}, H_{b2}, \ldots$ as a curve displacing three-dimensionally outside the incident plane A is determined from the measurement results of the second reflectances $R(\alpha_{b1}), R(\alpha_{b2}), \ldots$.

In the two intersections coordinate determining step, upon assuming a rectangular coordinate P-xyz in a space which has an x axis, a y axis and a z axis crossing at right angles and sharing the incident point P as an origin thereof, and of which an xy plane acts as a plane under measurement, and an xz plane inclusive of the incident point P acts as the incident plane A, intersections $Q_{li}(x_{li}, 0, z_i)$ and $Q_{mi}(X_{mi}, Y_{mi}, z_i)$ of a plane $z=z_i$ that is vertical to the z axis, and the first locus l and the second locus m are obtained.

In the model equation determining step, an approximation model equation in which a locus n (x, y, $z_i$) of a terminus of a bisection vector $H_i$ on the plane $z=z_i$ was modeled approximately from the intersections $Q_{li}$ and $Q_{mi}$ with an equation showing a smooth curve passing the intersections $Q_{li}$ and $Q_{mi}$ is determined.

In this case, the above-described smooth curve means the curve having no point at which differential is impossible. And examples of the smooth curves passing the above-described intersections $Q_{li}$ and $Q_{mi}$ include implicit function curves, explicit function curves, curves expressed by Fourier series, curves by liner bonding of orthogonal functions and parametric curves. In this case, the degree of these curves is not limited specifically provided that they are curves. And the parametric curves are curves of which each coordinate is expressed parametrically by a single parameter, and examples thereof include Bézier curves and spline curves. For example, It is preferable to adopt an elliptic curve as one of the implicit function curves having the secondary degree among these curves.

In the overall locus determining step, an overall locus n' (x, y, z) of the overall termini of a bisection vector H' between a reflected light V' other than the first reflected light $V_a$ and the second reflected light $V_b$, and the incident light $L_d$, is approximately determined from the above-described approximation model equation under the condition of $z_i=0\sim\infty$.

The displacement angles $\alpha_1, \alpha_2, \ldots$ include at least one displacement angle selected from N ($1\leq N\leq 89$) representative N displacement angles prescribed within the range of 0~90°.

And in the method for estimating reflectance in accordance with the present invention, the first reflectance measuring step, the first locus determining step, the second reflectance measuring step, the second locus determining step, the two intersections coordinate determining step, the model equation determining step and the overall locus determining step are repeated for each of the incident lights $L_d=L_1, L_2, \ldots$ at a plurality of incident angles $\theta_d=\theta_1, \theta_2, \ldots$ within the range of 0~90°.

In this case, the displacement angle α in the method for estimating reflectance in accordance with the present invention means an angle between a regularly reflected light S of an incident light L, which is regularly reflected inside the incident plane A when the incident light L is made incident on an incident point P on a plane under measurement at a predetermined incident angle θ, and a reflected light V of the incident light L, which is reflected and received from the incident point P, and this displacement angle α includes a displacement angle inside the incident plane A and a displacement angle outside the incident plane A.

And in the case of the displacement angle α being a displacement angle inside the incident plane (the xz plane extended between the x axis and the z axis in the rectangular coordinate P-xyz) A, the displacement angle α becomes positive on the side from the regularly reflecting direction toward a normal line (the z axis in the rectangular coordinate P-xyz) of the plane under measurement (the xy plane extended between the x axis and the y axis in the rectangular coordinate P-xyz) at an incident point, whereas it becomes negative on the side from the regularly reflecting direction toward the plane under measurement. On the other hand, in the case of the displacement angle α being a displacement angle outside the incident plane A, the displacement angle α becomes positive when both the x coordinate and the y coordinate of the bisection vector become greater than 0, whereas it becomes negative when the y coordinate becomes 0 or over and the x coordinate becomes less than 0.

And the bisection vector means a vector (halfway vector) which is directed in an direction of half of the angle between an incident light vector and a reflected light vector.

In the method for estimating a reflectance in accordance with the present invention, with the first reflectance measuring step and the first locus determining step, a first locus l of the reflectance $R(\alpha_a)$ of the first reflected light $V_a$ inside the incident plane A is obtained, and with the second reflectance measuring step and the second locus determining step, a second locus m of the reflectance $R(\alpha_b)$ of the second reflected light $V_b$ outside the incident plane A is obtained. At this time, the reflectance at the measurement point where the displacement angle α becomes negative is not measured, using the reciprocity in reflectance. And, in principle, the reflectance is measured at only the measurement point where the displacement angle α becomes a predetermined representative N displacement angles. The reflectance at the displacement angle other than the representative N displacement angles can be interpolated by the extrapolation process and the curve interpolation method, etc. of a principal component vector (eigenvector) obtained with the principal component analysis, the multi-regression analysis and the time-sequential analysis. And, with the two intersections coordinate determining step, the model equation determining step and the overall locus determining step, the reflected light distribution is modeled from the first locus l and the second locus m, thereby obtaining a three-dimensional reflected light distribution.

Therefore, with the method for estimating a reflectance in accordance with the present invention, the three-dimensional reflected light distribution can be obtained so that the reflectances at not only the displacement angle $\alpha$ inside the incident plane A but also the displacement angle $\alpha$ in three dimensions inclusive of the outside of the incident plane A can be estimated.

In addition, with the method for estimating a reflectance in accordance with the present invention, by using the reciprocity in reflectance and the modeling of the reflected light distribution, the measuring points can be reduced to shorten the measuring period of time, as compared with the all points measuring method, etc. of performing the measurement while varying all incident angles and all reflection angles, whereby the reflectance of even the color shifted painting color can be measured conveniently.

In the method for estimating a reflectance in accordance with the present invention, it is preferable in the second reflectance measuring step to measure the second reflectances $R(\alpha_{b1})$, $R(\alpha_{b2})$, ... of the second reflected lights $V_{b1}$, $V_{b2}$, ... on a conic plane of which an apex is taken as the incident point P, and a z axis as a rotation axis that is a normal line of the plane under measurement at the incident point P, and a generatrices make a similar angle to the incident angle $\theta_d$.

By taking the second reflected light $V_b$ on the conic plane making an angle $\theta_d$ with the z axis, in this manner, the measuring method becomes simple so that mistakes such as measurement omissions can be reduced upon measuring the reflectance $R(\alpha_b)$ of the second reflected light $V_b$ outside the incident plane A.

In the method for estimating a reflectance in accordance with the present invention, with the second reflectance measuring step, where planes $B_1$, $B_2$, $B_3$, ... making azimuth angles $\varnothing_1=90°$, $\varnothing_2=(90-e)°$, $\varnothing_3=(90-2e)°$, ... with an xz plane as the incident plane A, and including a z axis as the normal line of the plane under measurement at the incident point P are assumed (e is an arbitrary positive number), it is preferable to perform a first step of measuring the second reflectances $R(\alpha_{b1})$, $R(\alpha_{b2})$, ... of the second reflected lights $V_{b1}$, $V_{b2}$, ... such that the second bisection vectors $H_{b1}$, $H_{b2}$, ... exist inside the plane $B_1$ within the range in which the representative N displacement angles can be taken as many as possible, starting from a smaller angle, and, where in a (f−1) step just therebefore, at least one part of the second reflectances $R(\alpha_{b1})$, $R(\alpha_{b2})$, ... has not been measured, because at least one part of the representative N displacement angles has not been taken such that the second bisection vectors exist inside a plane $B_{f-1}$, and to repeatedly perform a f step of measuring the second reflectances $R(\alpha_{b1})$, $R(\alpha_{b2})$, ... of the second reflected lights $V_{b1}$, $V_{b2}$, ... such that the second bisection vectors $H_{b1}$, $H_{b2}$, ... exist inside not the plane $B_{f-1}$ but the plane $B_f$ within the range in which the representative N displacement angles, which has not been taken in the (f−1) step, can be taken as many as possible, starting from a smaller angle, as a second step, a third step, ..., thereby measuring the second reflectances $R(\alpha_{b1})$, $R(\alpha_{b2})$, ... of the second reflected lights $V_{b1}$, $V_{b2}$, ... are measured such that the second bisection vectors $H_{b1}$, $H_{b2}$, ... at the representative N displacement angles exist inside the plane $B_1$, $B_2$, $B_3$, ....

By measuring the reflectance $R(\alpha_b)$ of the second reflected light $V_b$ outside the incident plane A in the second reflectance measuring step in this manner, it is advantageous to separate the second locus m obtained in the second locus determining step from the first locus l so that the equation such as an ellipse, etc., which shows the reflected light distribution, can be specified more accurately, whereby the estimation of the reflectance can be performed with a higher precision.

In this case, in the method for estimating a reflectance in accordance with the present invention, the displacement angles $\alpha_1$, $\alpha_2$, ... include at least one displacement angle selected from N ($1 \leq N \leq 89$) representative N displacement angles prescribed within the range of 0 through 90° in order to reduce the measurement points, thereby shortening the measuring period of time.

The angle and the number of this representative N displacement angle are not limited specifically, but it is preferable that at least about 10° and about 90° are included from the viewpoint of enhancing the precision of the reflectance estimated with the method of the present invention, thereby improving the reliability, and the preferred representative N displacement angles are, for example, the representative five displacement angles of about 10° (10°±several degree), about 18° (18°±several degree), about 28° (28°±several degree), about 40° (40°±several degree), and about 90° (90°±several degree).

And, the reason why a negative displacement angle $\alpha$ is not considered as the representative N displacement angles is that the reciprocity in reflectance can be used. According to the reciprocity in reflectance, for example, the reflectance R(30, 70) of a reflected light in the case of the incident angle $\theta_a$ being 30°, and the displacement angle $\alpha$ inside the incident plane A being −40° (light receiving angle (=incident angle−displacement angle) $\theta_b$ is 70°) and the reflectance R(70, 30) of a reflected light in the case of the incident angle $\theta_a$ being 70°, and the displacement angle $\alpha$ inside the incident plane A being 40° (light receiving angle $\theta_b$ is 30°) become equal to each other (R(30, 70)=R(70, 30)). Consequently, the reflectance R(30, 70) of a reflected light in the case of the incident angle $\theta_a$ being 30°, and the displacement angle $\alpha$ inside the incident plane A being −40° (light receiving angle $\theta_b$ is 70°) is measured as the reflectance R(70, 30) of a reflected light in the case of the incident angle $\theta_a$ being 70°, and the displacement angle $\alpha$ inside the incident plane A being 40° (light receiving angle $\theta_b$ is 30°) so that the measurement thereof is unnecessary.

When an incident light or a reflected light enters within the angular range in which the angle with the plane under measurement (elevation angle from the plane under measurement) becomes less than a prescribed value (measurement impossible range), the measurement may become impossible due to structural limitations according to a measuring machine for use in measuring the reflectance. In this case, the reflectance of the incident light or the reflected light in the measurement impossible range can be replaced with the reflectance of a measurable light, which is closest to the same.

Upon using a measuring machine of which the measurement impossible range is the range where the angle with the plane under measurement is less than 10°, for example, when the incident angle exceeds 80°, the incident light enters the measurement impossible range so that the measurement of the reflectance becomes impossible. Therefore, in such a case, the reflectance of the incident light of which the incident angle exceeds 80° is not measured, but the reflectance of the incident light of which the incident angle is 80°, for example, can be selected in place thereof.

Similarly, upon using a measuring machine of which the measurement impossible range is the range where the angle with the plane under measurement is less than 10°, for example, when the incident angle becomes less than 10°, the reflected light of which the displacement angle α inside the incident plane becomes 90° enters the measurement impossible range so that the measurement of the reflectance becomes impossible. Therefore, in such a case, the reflectance of the reflected light of which the displacement angle α inside the incident plane is 90° at the incident angle θ less than 10°, for example, is not measured, but the reflectance of the reflected light of which the displacement angle α inside the incident plane is (80+θ)° at the incident angle θ less than 10° can be taken, for example, in place thereof.

In a preferred embodiment of the method for estimating a reflectance in accordance with the present invention, a color shifted painting color is applied to the plane under measurement. Namely, the method for estimating a reflectance in accordance with the present invention can be preferably used to measure the reflectance of the color shifted painting color.

In this case, the color shifted painting color means the color of which the displacement angle characteristics vary according to the incident angle of light (exhibiting incident angle dependence), and also vary according to the positive or negative of the displacement angle (exhibiting no symmetric properties in displacement angle characteristics at the displacement angle of 0°).

The displacement angle characteristics are the variations of the intensity of the reflected light due to the displacement angle (the angle between the regularly reflected light reflected inside the incident plane in the regularly reflecting direction, and the received reflected light).

OPERATIONAL EFFECT OF THE INVENTION

In accordance with the method for estimating a reflectance of the present invention, the measurement period of time can be shortened due to the decrement of the measurement points, as compared with the all points measuring method of performing the measurement while varying all incident angles and all reflected angles, whereby the reflectance of even the color shifted painting color can be measured conveniently.

EXPLANATION OF REFERENCE CHARACTERS

Figure 1:
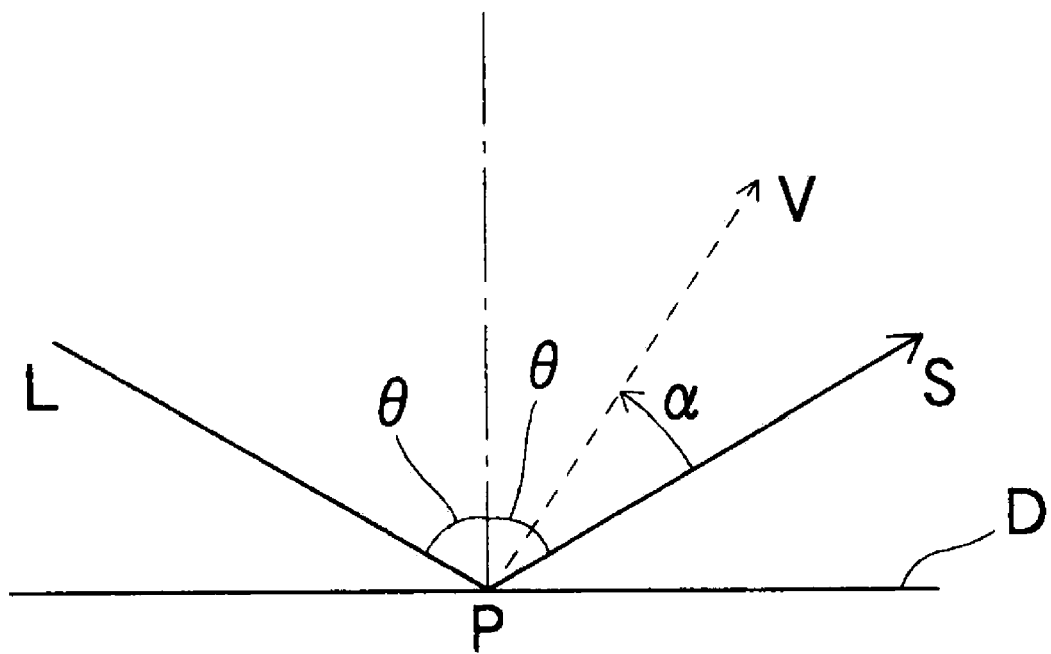
FIG. 1 is a diagram explaining the state where an incident light L is made incident on an incident point P on a plane D under measurement, which has been coated with a color shifted painting color, at a predetermined incident angle θ, and a reflected light V thereof is received, in Embodiment 1.

A . . . incident plane
D . . . plane under measurement
L . . . incident light
V . . . reflected light
S . . . regularly reflected light
θ . . . incident angle
l . . . first locus
m . . . second locus
$V_a$ . . . first reflected light
$V_b$ . . . second reflected light
$H_a$ . . . first bisection vector
$H_b$ . . . second bisection vector
α . . . displacement angle

BEST MODE FOR CARRYING OUT THE INVENTION

First, hereinafter, we will explain that in order to reduce the number of measuring points upon measuring a reflectance of a color shifted painting color, two techniques of the reciprocity in reflectance of a painting color, and modeling (numerically modeling) of a reflected light distribution are effective, along with results of the present inventor's studies and searches.

(Reduction of the Number of Measuring Points with the Reciprocity in Reflectance of Painting Color)

The reciprocity in reflectance of a painting color indicates the property that the reflectance of the painting color does not vary when an incident light and a reflected light are reversed to each other. Namely, where the reflectance $R(\theta a, \theta b)$ in the case of the incident angle of the incident light being $\theta a$, and the receiving angle (=incident angle−displacement angle) of the reflected light being $\theta b$ is equal to the reflectance $R(\theta b, \theta a)$ in the case of the incident angle being $\theta b$, and the receiving angle being $\theta a$ with the incident light and the reflected light reversed ($R(\theta a, \theta b)=R(\theta b, \theta a)$), the reflectance of the painting color is considered to exhibit reciprocity.

In order to confirm whether there is reciprocity in reflectance with respect to the painting color or not, color differences of 194 kinds of the above-described sample painting colors inclusive of the color shifted painting color were calculated with the incident angle and the receiving angle interchanged inside the incident plane. More specifically, color differences of two sets of R(45, 60) and R(60, 45), and R(50, 60) and R(60, 50) were calculated for each painting color. As a result, the average color difference between R(45, 60) and R(60, 45) was as small as 2.10, whereas the average color difference between R(50, 60) and R(60, 50) was as small as 1.86.

In addition, by examining the reflectances of the above-described sample painting colors with the incident angle and the receiving angle interchanged within the range of 15 to 141° in the case of no reflected light existing inside the incident plane of the incident light, it was confirmed that there was reciprocity in reflectance of the painting color even in the case of no reflected light existing inside the incident plane.

These results show that in either one of the color shifted painting color and the general painting color, there is reciprocity in reflectance. Consequently, it has been clarified that the number of measuring points can be reduced by 50% using the reciprocity.

(Reduction of the Number of Measuring Points with the Modeling of the Reflected Light Distribution)

And, the present inventor has studied and researched on the reduction of the number of the measuring points by numerically modeling the reflected light distribution.

If the distribution of reflected lights itself at each incident angle is tried to be shown in the drawing, upon considering the distribution of the reflected lights, the direction of the distribution of the reflected lights varies according to the incident angle so that it becomes difficult to compare the distribution of the reflected lights at each incident angle.

Under the above circumstances, the present inventor has decided to consider the reflectance with a model of microfacets using bisection vectors (a plane assumed to be composed of microfacets with different directions, and is composed of a plurality of small element planes). With this microfacet model, the intensity of the reflected light can be considered for convenience to be in proportion to the number of the microfacets directed toward the bisection vector between the incident light and the reflected light (direction angled by half of the angle between the incident light and the reflected light). In this case, upon showing the distribution of the microfacets at each incident angle, the distribution of the microfacets is constantly directed upwardly regardless of the variation of the incident angle so that the comparison thereof becomes easy.

Figure 9:
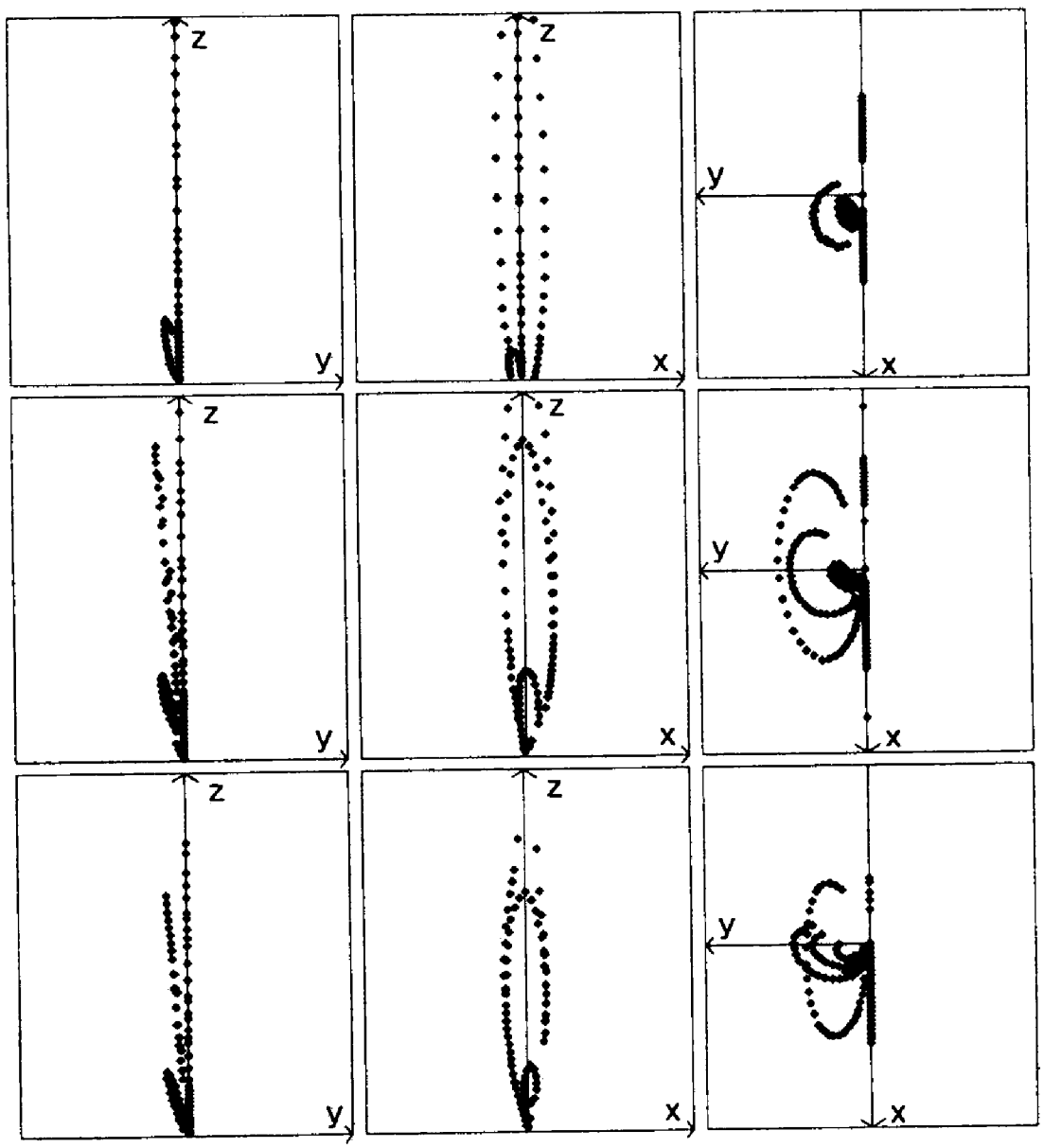
FIG. 9 stereoscopically shows the reflection distributions of an incident light with a wavelength of 390 nm by the distribution of microfacets, upper three show those at the incident angle of 20°, middle three show those at the incident angle of 40°, and lower three show those at the incident angle of 60°. And left columns show yz planes, central columns show zx planes and right columns show xy planes.

Therefore, in order to examine the reflection distribution of the color shifted painting color, the present inventor has shown the distribution of the microfacets in the case of the incident angle of a light source being varied. FIG. 9 stereoscopically shows the reflection distribution of an incident light with a wavelength of 390 nm by the distribution of the microfacets, three in an upper row show those at the incident angle of 20°, three in a middle row show those at the incident angle of 40°, and three in a lower row show those at the incident angle of 60°. And in FIG. 9, a left column shows a yz plane, a central column shows a zx plane and a right column shows an xy plane. In this case, FIG. 9 shows the reflection distribution of the reflected light when a light receiving displacement angle is positive. The reflection distribution of the reflected light when the light receiving displacement angle is negative becomes the reflection distribution obtained when the light receiving displacement angle is positive by interchanging the reflected light and the incident light when the light receiving displacement angle is negative by virtue of the reciprocity in reflectance.

It has become clear from FIG. 9 that, with respect to the color shifted painting color, the distribution of the microfacets, which is obtained when the incident angle of the light source is varied, can be approximated with one part of an ellipsoid. More specifically, upon assuming a rectangular coordinate P-xyz having an x axis, a y axis and a z axis which cross at right angles and share the incident point P as an origin, and existing in a space in which the plane under measurement becomes an xy plane, and an xz plane inclusive of the incident point P becomes the incident plane A, one part of the ellipsoid, which approximately shows the distribution of the microfacets when the incident angle of the light source is varied in the case of the light receiving displacement angle being positive, becomes one part of an ellipse having a center at the incident point P, and having a major axis and a minor axis in the x axis and the y axis (or y axis and x axis) in the plane of $z=z_i$.

Where the light receiving displacement angle is negative, the distribution of the microfacets, which is obtained when the incident angle of the light source is varied, can be approximated with one part of an ellipsoid having a center at the incident point P, and having a major axis and a minor axis in the x axis and the y axis (or y axis and x axis) in the plane of $z=z_i$, similarly to the case where the light receiving displacement angle is positive, but it is unnecessary to consider the same, by using the reciprocity in reflectance.

It is considered that the reason why the microfacets in the color shifted painting color are distributed in the above-described ellipsoid is that a Lambert's low's circle deforms with a special bright material and a special layered structure. On the other hand, with respect to the general painting color other than the color shifted painting color, it is considered that as the distribution of the reflected light is symmetric rotationally with the regularly reflected light, the distribution of the microfacets becomes a figure symmetric rotationally with respect to a normal line on a surface.

It has become clear from these results that by considering the distribution of the microfacets with the bisection vector of the incident light entering the plane under measurement to which the color shifted painting color has been applied, and a reflected light thereof, the reflection distribution of the reflected light reflected from the plane under measurement can be modeled with a numerical equation. Namely, it has become clear that upon taking note of one part of the above-described ellipsoid having a center at an incident point, which approximately illustrates the distribution of the microfacets in the color shifted painting color, that is one part of an ellipse taken along a plane parallel to the plane under measurement (an ellipse of which a center is on a normal line at an incident point of the plane under measurement), the reflection distribution of the color shifted painting color can be approximately modeled from the numerical equation showing that ellipse.

In this case, the ellipse of which a center is known can be specified with a numerical equation if coordinates of two points on the ellipse are known. For example, the ellipse which passes two points (a, 0) and (0, b) in an xy coordinate, and of which a center is an origin thereof can be specified with the equation $(x/a)^2+(y/b)^2=1$.

Under the above circumstances, in order to specify one part of the above-described ellipsoid having a center at an incident point, which approximately illustrates the distribution of the microfacets in the color shifted painting color, that is one part of an ellipse taken along a plane parallel to the plane under measurement (an ellipse of which a center is on a normal line at an incident point of the plane under measurement), with a numerical equation, the present inventor has contemplated defining the magnitude of the reflectance as the length of the bisection vector of the reflected light, obtaining a locus of termini of bisection vectors of reflected lights inside an incident plane and a locus of termini of bisection vectors of reflected lights outside the incident plane, and obtaining intersections of the respective loci and the above-described plane.

The locus of the bisection vectors inside the incident plane can be obtained by measuring the reflectance of the reflected light when the displacement angle α is varied inside the incident plane. Therefore, even where the reflectances of the reflected lights at representative displacement angles inside the incident plane are measured for interpolation, with the above-described conventional five angles method, the locus with some high reliability can be obtained.

However, where the locus of the bisection vectors outside the incident plane is obtained, there have been exhibited various problems.

First, since the above-described conventional five angles method is used to measure the reflectances of the reflected lights inside the incident plane at representative displacement angles, it has not become clear whether the locus obtained after interpolated by measuring the reflectances of the reflected lights at the representative displacement angles outside the incident plane exhibits reliability or not.

Under the above circumstances, the present inventor has considered that where an incident light enters an incident point P on a plane under measurement inside an incident plane A at an incident angle θ, a reflected light $V_b$ exists on a conic plane of which an apex is the incident point P on the plane under measurement, and a z axis as a rotation axis serving as a normal line of the plane under measurement and a generatrices make a similar angle to the incident angle θ. In this case, where an azimuth angle Ø between the incident plane A and a reflection plane is used, the reflected light $V_b$ on the conic plane which makes an angle θ with the z axis is expressed by the equation: $V_b$=(sin θ cos Ø, sin θ sin Ø, cos θ). And by taking the displacement angle α between the regularly reflected light S and the reflected light $V_b$ inside the incident plane A as representative five displacement angles of 10°, 18°, 28°, 40° and 90°, the reflectance $R(\alpha_b)$ of the reflected light $V_b$ at each of the representative five displacement angles is measured, and calculated reflectance values interpolated from the measurement results, and actually measured reflectance values at the respective representative displacement angles α were compared with each other.

Figure 10:
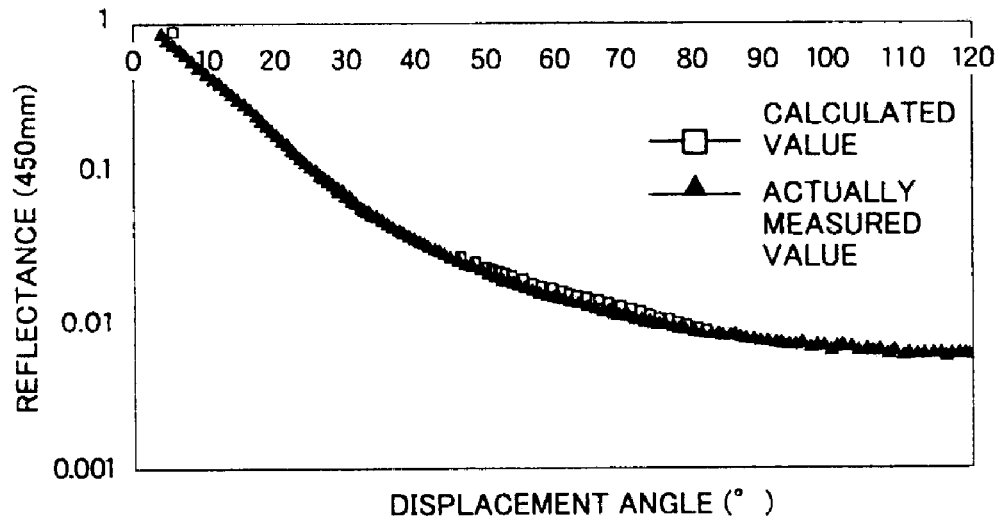
FIG. 10 (a) shows comparison results of calculated values and actually measured values of the reflectance in the case of the wavelength being 450 nm and the incident angle θ being 60°, (b) shows a color difference therebetween at each displacement angle α.
Figure 10:
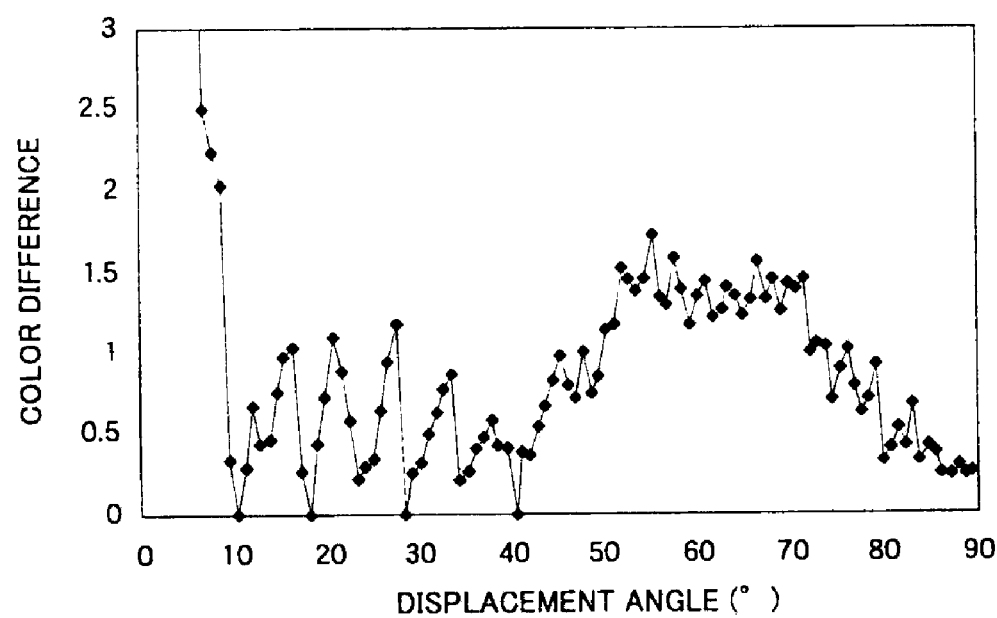

In the case of the wavelength being 450 nm and the incident angle θ being 60°, the comparison results between the calculated reflectance values and the actually measured reflectance values are shown in FIG. 10(a), and a color difference therebetween at each displacement angle α is shown in FIG. 10(b). It has become clear from FIG. 10 that when the displacement angle α is 10° or more, the color difference becomes 2 or less, and that the calculated reflectance values and the actually measured reflectance values are approximately equal to each other. In the case of other incident angles and other wavelengths, the calculated values and the actually measured values have become approximately equal to each other.

It has become clear from these results that the above-described conventional five angles method also stands when the reflectances at representative displacement angles outside the incident plane are measured.

In addition, from the viewpoint of the improvement of the reliability of the numerical equation indicating an ellipse, it is desirable that the locus of the termini of the bisection vectors of the reflected lights inside the incident plane and the locus of the termini of the bisection vectors of the reflected lights outside the incident plane are spaced from each other as far as possible. From this viewpoint, it is desirable that the bisection vector of the reflected light outside the incident plane is on a plane vertical to the incident plane, for example, that is on a plane at an azimuth angle Ø of 90° with the incident plane.

However, as describing later, in the case of the incident angle θ being constant, the range of the representative displacement angles, in which the bisection vector can exist on the plane at an azimuth angle Ø of 90°, is the narrowest, and as the azimuth angle Ø decreases from 90°, the range of the representative displacement angles, in which the bisection vector can exist on the plane at that azimuth angle Ø enlarges. In other words, on the plane at an azimuth angle Ø of 90°, the range of the incident angle θ, in which the bisection vectors at all representative displacement angles can exist on that plane, becomes narrow, and as the azimuth angle Ø decreases from 90°, the range of the incident angle θ, in which the bisection vectors at all representative displacement angles can exist on that plane, enlarges. Therefore, it is not always effective to obtain a locus of termini of bisection vectors existing on the plane at the azimuth angle Ø of 90° as the locus of the termini of the bisection vectors of the reflected lights outside the incident plane.

Accordingly, in order to obtain the locus of the termini of the bisection vectors of the reflected lights outside the incident plane, the present inventor has contemplated two techniques for obtaining the locus of the termini of the bisection vectors, as a curve displacing three-dimensionally outside the plane at the azimuth angle Ø of 90°, and have confirmed that they are effective.

Hereinafter, embodiments of the method for estimating a reflectance in accordance with the present invention, which has been made based on the above-described results of studies and researches, will be explained with reference to the drawings.

Embodiment 1

In accordance with the method for estimating a reflectance of the present embodiment, as shown in FIG. 1, when an incident light L is made incident on an incident point P of a plane under measurement D, which is coated with a color shifted painting color, at an incident angle θ, and a reflected light V is received, the reflectance at an arbitrary displacement angle inside an incident plane A and outside the incident plane A is estimated by taking an angle between a regularly reflected light S resulted from the regularly reflecting of the incident light L inside the incident plane A, and the reflected light V as the displacement angle α. In this case, the reflected light V includes both a reflected light reflected inside the incident plane A and a reflected light reflected outside the incident plane A.

Hereinafter, the case where the incident angle $\theta_d$ is varied by every 1° in the range of 0~90° such that the incident angle $\theta_d$ has the condition of $\theta_1$, $\theta_2$, . . . =0°, 1°, 2° . . . will be explained, but the angle by which the incident angle $\theta_d$ is varied is not limited specifically.

And, hereinafter, the case where a measuring machine which cannot be measured in an angular range of less than 10° is used will be explained, but this angular range is not limited specifically. In this case, "cannot be measured in an angular range of less than 10°" means that when the incident light L or the reflected light V enters the angular range (measurement impossible range) in which the angle with the plane under measurement D (elevation angle from the plane under measurement D) is less than 10°, the measurement becomes impossible due to the structural limitations of the measuring machine.

Hereinafter, each step will be explained specifically.

<First Reflectance Measuring Step>

Figure 2:
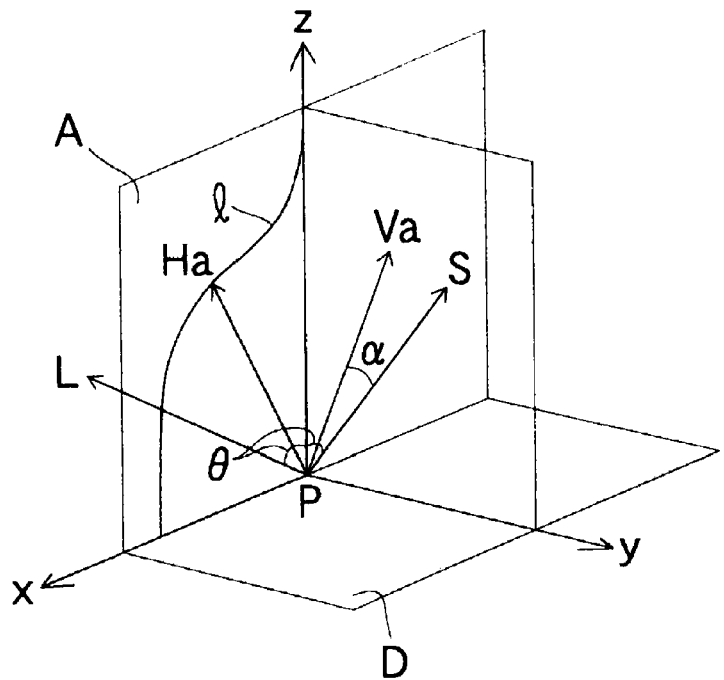
FIG. 2 is a diagram explaining the state where when an incident light $L_d$ is made incident on an incident point P on a plane D under measurement, which has been coated with a color shifted painting color, at an incident angle $θ_d$, and a light is received at a predetermined displacement angle α inside the incident plane A, a first reflectance (spectral steric angle reflectance) $R(α_a)$ of a first reflected light $V_a$ inside the incident plane A is measured in a first reflectance measuring step in Embodiment 1.

In the first reflectance measuring step, when, as shown in FIG. 2, an incident light $L_d$ is made incident on the incident point P of the plane under measurement D which has been coated with a color shifted painting color, at an incident angle $\theta_d$, and light is received at a predetermined displacement angle α inside the incident plane A, a first reflectance (spectral steric angle reflectance) $R(\alpha_a)$ of a first reflected lights $V_a$ inside the incident plane A is measured.

Namely, in this first reflectance measuring step, the incident light $L_d$ is made incident on the incident point P of the plane under measurement D, which has been coated with color shifted painting color, at an incident angle $\theta_d$. And first reflectances $R(\alpha_{a1})$ $R(\alpha_{a2})$ of first reflected lights $V_{a1}$, $V_{a2}$ . . . inside the incident plane A against the incident light $L_d$ are measured when light is received at predetermined displacement angles $\alpha_1$, $\alpha_2$, . . . inside the incident plane A.

In the present embodiment, as shown in Table 1, $(80+\theta_d)°$ is selected other than the representative five displacement angles of 10°, 18°, 28°, 40° and 90° as the measurement displacement angles $\alpha_1$, $\alpha_2$, . . . for measuring the first reflectances $R(\alpha_{a1})$, $R(\alpha_{a2})$ in the first reflectance measuring step. And, the measurement displacement angles that can be measured according to the magnitude of the incident angle $\theta_d$ are selected among them.

Namely, when the incident angle $\theta_d$ ranges from 10 to 80° ($\theta_d$=10°, 11°, . . . , 80°), all of the representative five displacement angles of 10°, 18°, 28°, 40° and 90° are selected as the measurement displacement angles $\alpha_1$, $\alpha_2$, . . . .

And when the incident angle $\theta_d$ ranges from 0 to 9° ($\theta_d$=0°, 1°, . . . , 9°), four points of 10°, 18°, 28° and 40° among the representative five displacement angles, and $(80+\theta_d)°$ are selected as the measurement displacement angles $\alpha_1$, $\alpha_2$, . . . . Namely, when the incident angle $\theta_d$ ranges from 0 to 9°, the reflectance at the displacement angle α of $(80+\theta_d)°$ is measured in place of the measurement of the reflectance at the displacement angle of 90° as the representative five displacement angles.

In this case, the reason why $(80+\theta_d)°$ is selected as the measurement displacement angle α in place of 90° as the representative five displacement angles when the incident angle $\theta_d$ ranges from 0 to 9° is that the first reflected light $V_a$ reflected inside the incident plane A at the displacement angle α=90° when the incident angle $\theta_d$ ranges from 0 to 9° enters the above-described measurement impossible range, and consequently, the reflectance thereof cannot be measured.

In addition, when the incident angle $\theta_d$ ranges from 81 to 90° ($\theta_d$=81°, 82°, . . . , 90°), the incident light $L_d$ enters the above-described measurement impossible range, and consequently, the reflectance of the first reflected light $V_a$ thereof cannot be measured. For this reason, in the present embodiment, with respect to the incident light $L_d$ of which the incident angle $\theta_d$ ranges from 81 to 90°, the first reflected light $V_a$ thereof is not measured, but calculated using the reflectance of the first reflected light $V_a$ of the incident light $L_d$ of which the incident angle $\theta_d$ is 80°.

In this case, with respect to the measurement point at which the displacement angle α becomes negative, the reflectance is not measured based on the reciprocity in reflectance.

Therefore, the total of the measurement points at which the first reflectances $R(\alpha_a)$ are to be measured in the first reflectance measuring step in the present embodiment is 5×81=405 (points).

TABLE 1

| First reflectance measuring step (inside incident plane A) | | |
|---|---|---|
| Incident angle $\theta_d$ (°) | Number of measurement displacement angles | Angle (°) of measurement displacement angle |
| 81~90 | — | — |
| 10~80 | 5 | 10, 18, 28, 40, 90 |
| 0~9 | 5 | 10, 18, 28, 40, 80 + $\theta_d$ |

<First Locus Determining Step>

In the first locus determining step, a first locus l of termini of first bisection vectors $H_{a1}$, $H_{a2}$, . . . , as a curve displacing two-dimensionally inside the incident plane A, is obtained from the measurement results of the first reflectances $R(\alpha_{a1})$, $R(\alpha_{a2})$, . . . obtained in the above-described first reflectance measuring step.

This first bisection vector $H_{a1}$, $H_{a2}$, . . . is the bisection vector between each of the first reflected lights $V_{a1}$, $V_{a2}$, . . . inside the incident plane A and the above-described incident light $L_d$. And in this first bisection vector $H_{a1}$, $H_{a2}$, . . . , the magnitude of each of the first reflectances $R(\alpha_{a1})$, $R(\alpha_{a2})$ is defined as the length of each of the first bisection vectors $H_{a1}$, $H_{a2}$, . . . , that is $|H_{a1}|=|R(\alpha_{a1})|$, $|H_{a2}|=|R(\alpha_{a2})|$, . . . .

Therefore, the first locus l of the termini of the first bisection vectors $H_{a1}$, $H_{a2}$, . . . becomes a curve displacing two-dimensionally inside the incident plane A. And this first locus l approximately shows the reflection distribution of the first reflected lights $V_{a1}$, $V_{a2}$, . . . at each incident angle $\theta_d$.

In this case, as shown in FIG. 2, where a rectangular coordinate P-xyz existing in a space in which a plane under measurement D is an xy plane, and a normal line of this plane under measurement D at the incident point P is a z axis is assumed, the incident plane A becomes an xz plane. And one end of the first locus l becomes a point on the z axis (terminus of the first bisection vector $H_a$ at the displacement angle α of 0°). In addition, the other end of the first locus l may become a point located on an incident light vector L (terminus of the first bisection vector $H_a$ at the displacement angle α of $2\theta_d°$) or the other end side of the first locus l may pass the point on the incident light vector L (terminus of the first bisection vector $H_a$ at the displacement angle α of $2\theta_d°$).

Upon obtaining the first locus l, the reflectance at the displacement angle other than the measurement points (measurement displacement angles) at which the reflectance was measured in the first reflectance measuring step can be interpolated mainly with the principal component analysis.

The reflectance of the plane under measurement depends on the measurement displacement angle, but with the principal component analysis of the reflectances at a plurality of predetermined displacement angles, features of the reflectance can be obtained, and the reflectance at the displacement angle other than the predetermined displacement angles can be estimated from feature amounts of the reflectance. Namely, by performing the principal component analysis of the reflectance at the measurement displacement angles, obtaining a principal component obtained with the analysis results as an eigenvalue, obtaining a principal component vector as an eigenvector, and determining a basic equation expressed by these eigenvalue, eigenvector and a coefficient to be multiplied on the eigenvector, the reflectance at the displacement angle other than the measurement points can be estimated from this basic equation.

Hereinafter, the principle of the estimation of reflectance with the principal component analysis will be briefly explained.

The reflectance at the displacement angle $\alpha_1, \alpha_2, \ldots, \alpha_p$ in the case of the wavelength being $\lambda i$ is expressed by a vector value $X^i$ having p elements shown in the following equation (4):

$$X^i = (\rho^i_1, \rho^i_2, \ldots, \rho^i_p)^T \quad (4)$$

And, by assuming that there are N samples of $X^i$, a j-th sample $X^i_j$ is expressed by the following equation (5):

$$X^i_j = (\rho^i_{1j}, \rho^i_{2j}, \ldots, \rho^i_{pj})^T \quad (5)$$

And, the eigenvalues obtained by the principal component analysis of N samples $X^i_j$ (j=1, 2, ..., N) are expressed by $l_1, l_2, \ldots, l_p$ ($l_1 > l_2 > \ldots > l_p$), and the eigenvector corresponding thereto are expressed by $b^i_1, b^i_2, \ldots, b^i_p$. In this case, $b^i_j$ is assumed by the following equation (6):

$$b^i_j = (b^i_{1j}, b^i_{2j}, \ldots, b^i_{pj})^T \quad (6)$$

As a result, as shown in the following equation (7), $X^i_j$ can be reconstructed with a vector $u^i$, an eigenvector $b^i$ and a coefficient $k^i$, which have been obtained by the principal component analysis, based on the principle of the principal component analysis.

$$X^i_j = u^i + k^i_{1j}b^i_1 + k^i_{2j}b^i_2 + \ldots + k^i_{pj}b^i_p \quad (7)$$

In this case, the vector $u^i$ is an average vector expressed by the following equation (8):

$$u^i = (u^i_1, u^i_2, \ldots, u^i_p)^T \quad (8)$$

wherein:

$$u^i_l = \frac{1}{N}\sum_{m=1}^{N} \rho^i_{lm} \quad (9)$$

And the eigenvector $b^i$ is a p dimension orthogonal base satisfying a characteristic equation expressed by the following equation (10):

$$R^i b^i_j = 1^i_j b^i_j, j=1,2,\ldots,p \quad (10)$$

In this case, $R^i$ is a co-dispersion matrix expressed by the following equation (11):

$$R^i = \begin{pmatrix} c^i_{11} & c^i_{12} & \cdots & c^i_{1p} \\ c^i_{21} & c^i_{22} & \cdots & c^i_{2p} \\ \vdots & \vdots & \ddots & \vdots \\ c^i_{p1} & c^i_{p2} & \cdots & c^i_{pp} \end{pmatrix} \quad (11)$$

In this case, $c^i$ in the equation (11) is expressed by the following equation (12).

$$c^i_{kj} = \frac{1}{N-1}\sum_{n=1}^{N}(\rho^i_{nk} - u^i_k)(\rho^i_{nj} - u^i_j) \quad (12)$$

In addition, the coefficient $k^i_j$ is expressed by the following equation (13):

$$k^i_{ij} = b^i_{ij}{}^T X^i_j \quad (13)$$

The above-described equation (7) uses a first principal component through a p-th principal component, but in the principal component analysis, a first principal component through a m-th principal component can be expressed using m less than p. This can be written as the following equation (14) in element expression.

$$\begin{pmatrix} \rho^i_{1j} \\ \rho^i_{2j} \\ \vdots \\ \rho^i_{pj} \end{pmatrix} = \begin{pmatrix} u^i_1 \\ u^i_2 \\ \vdots \\ u^i_p \end{pmatrix} + k^i_{1j}\begin{pmatrix} b^i_{11} \\ b^i_{21} \\ \vdots \\ b^i_{p1} \end{pmatrix} + \ldots + k^i_{mj}\begin{pmatrix} b^i_{1m} \\ b^i_{2m} \\ \vdots \\ b^i_{pm} \end{pmatrix} \quad (14)$$

As will be understood from the above-described equation (14), the reflectance $\rho$ at an arbitrary displacement angle $\alpha$ can be expressed by the average vector u, the eigenvector b and the coefficient k. Consequently, by determining the coefficient k using the reflectances at the representative five displacement angles etc., which have been measured with respect to the plane under measurement, the reflectance at the displacement angle other than the measurement points can be derived from the above-described equation (14). By solving this equation (14) for the coefficient k, the following equation (15) can be obtained.

$$\begin{pmatrix} k^i_{1j} \\ k^i_{2j} \\ \vdots \\ k^i_{pj} \end{pmatrix} = \begin{pmatrix} b^i_{11} & b^i_{12} & \cdots & b^i_{1m} \\ b^i_{21} & b^i_{22} & \cdots & b^i_{2m} \\ \vdots & \vdots & \ddots & \vdots \\ b^i_{p1} & b^i_{p2} & \cdots & b^i_{pm} \end{pmatrix}^{-1} \begin{pmatrix} \rho^i_{1j} - u^i_1 \\ \rho^i_{2j} - u^i_2 \\ \vdots \\ \rho^i_{pj} - u^i_p \end{pmatrix} \quad (15)$$

In this case, by expressing the reflectances at the representative five displacement angles by $\rho^i_{1j}, \rho^i_{2j}, \ldots, \rho^i_{5j}$, for example, and considering the first through fifth principal components in the above-described equation (7), the following equation (16) stands for these five displacement angles.

$$\begin{pmatrix} \rho^i_{1j} \\ \rho^i_{2j} \\ \vdots \\ \rho^i_{5j} \end{pmatrix} = \begin{pmatrix} u^i_1 \\ u^i_2 \\ \vdots \\ u^i_5 \end{pmatrix} + k^i_{1j} \begin{pmatrix} b^i_{11} \\ b^i_{21} \\ \vdots \\ b^i_{51} \end{pmatrix} + \ldots + k^i_{5j} \begin{pmatrix} b^i_{15} \\ b^i_{25} \\ \vdots \\ b^i_{55} \end{pmatrix} \quad (16)$$

By solving this equation (16) for the coefficient $k^i_1, k^i_2, \ldots, k^i_5$, the following equation (17) can be obtained.

$$\begin{pmatrix} k^i_{1j} \\ k^i_{2j} \\ \vdots \\ k^i_{5j} \end{pmatrix} = \begin{pmatrix} b^i_{11} & b^i_{12} & \ldots & b^i_{15} \\ b^i_{21} & b^i_{22} & \ldots & b^i_{25} \\ \vdots & \vdots & \ddots & \vdots \\ b^i_{51} & b^i_{52} & \ldots & b^i_{55} \end{pmatrix}^{-1} \begin{pmatrix} \rho^i_{1j} - u^i_1 \\ \rho^i_{2j} - u^i_2 \\ \vdots \\ \rho^i_{5j} - u^i_5 \end{pmatrix} \quad (17)$$

By obtaining $k^i_1, k^i_2, \ldots, k^i_5$ from this equation, and substituting them in the above-described equation (16), the reflectance at the displacement angle other than the measurement points such as the representative five displacement angles, etc. can be estimated.

In addition, ten reflectances at the displacement angle $\alpha$ of 0 through 9° ($\alpha=0°, 1°, \ldots, 9°$) involve a large error so that even if the reproduction is faithfully performed according to the measured values, the reproduction results are low in reliability. However, where an image display such as CG is performed, the data concerning the reflectance at all displacement angles are needed, and the data of the reflectance at the displacement angle less than 10° is also needed. At this time, in order to improve the smooth continuity of the image display in CG, etc, it is desirable to estimate the data of the reflectance at the displacement angle $\alpha$ of less than 10° such that the reflection characteristics are smoothly continuous with the tendency of the reflection characteristics at the displacement angle $\alpha$ of 10 to 90° while maintaining the same.

Therefore, in the present embodiment, by performing the time-sequential analysis based on the data of the reflectances at the displacement angle $\alpha$ of 10 to 90°, the reflectance at the displacement angle $\alpha$ ranging from 0 to 9° is estimated. It is preferable that this extrapolation with the time-sequential analysis is not directly performed against the reflectance, but performed against five principal component vectors at the displacement angle ranging from 0 to 9°. If the five principal component vectors at the displacement angle ranging from 0 to 9° can be formed, the reflectance at the displacement angle ranging from 0 to 9° can be estimated from the above-described equation (16) and the extrapolation can be performed.

In the time-sequential analysis, when the time-sequential data $x_t$ against $t=1, 2, \ldots, n$ is given, $x_t$ for $t=n+1, n+2, \ldots$ can be estimated by analyzing these time-sequential data and formulating the same. Upon analyzing, Box-Jenkins method enabling the steady execution of the formulation, for example, can be used.

In order to estimate the reflectance at the displacement angle $\alpha$ less than 10°, the multi-regression analysis and the curve interpolation method, etc. can be used other than the above-described time-sequential analysis.

And in the range where the displacement angle $\alpha$ exceeds 90°, the reflectance scarcely varies so that it can be approximated by the reflectance at the displacement angle $\alpha$ of 90° without measuring the reflectance.

In this case, the first reflected light $V_a$ at the displacement angle $\alpha$ of 0° is a regularly reflected light $S_d$ obtained when the incident light $L_d$ reflects inside the incident plane A in a regularly reflecting direction. And, the terminus of the first bisection vector $H_a$ of the first reflected light $V_a$ as the regularly reflected light $S_d$ becomes one end of the first locus l obtained in the first locus determining step. And, the first reflected light $V_a$ at the displacement angle $\alpha$ of $2\theta_d°$ becomes a reflected light reflecting in an incident direction (toward a light emergent side, namely, in a recurrent reflecting direction), but the terminus of the first bisection vector $H_a$ of the first reflected light $V_a$ at the displacement angle $\alpha$ of $2\theta_d°$ becomes a point on an incident light vector L. In this case, one of the first locus l (a terminus of a first bisection vector $H_a$ of the first reflected light $V_a$ at the displacement angle $\alpha$ of 0°) coincides with one end of the second locus m (a terminus of a second bisection vector $H_b$ of the second reflected light $V_b$ at the displacement angle $\alpha$ of 0°) obtained in the second locus determining step. And one point of the first locus l located on an incident light vector L (terminus of the first bisection vector $H_a$ of the first reflected light $V_a$ at the displacement angle $\alpha$ of $2\theta_d°$) coincides with the other end of the second locus m (terminus of the second bisection vector $H_b$ of the second reflected light $V_b$ at the displacement angle $\alpha$ of $2\theta_d°$) obtained in the second locus determining step.

<Second Reflectance Measuring Step>

In the second reflectance measuring step, an incident light $L_d$ is made incident on the incident point P of the plane under measurement D at an incident angle $\theta_d$, and a second reflectance $R(\alpha_b)$ of a second reflected light $V_b$ outside the incident plane A is measured when light is received at a predetermined displacement angle $\alpha$ outside the incident plane A.

Namely, in this second reflectance measuring step, the incident light $L_d$ is made incident on the incident point P of the plane under measurement D at an incident angle $\theta_d$ inside the incident plane A. And second reflectances $R(\alpha_{b1})$, $R(\alpha_{b2}), \ldots$ of second reflected lights $V_{b1}, V_{b2} \ldots$ outside the incident plane A relative to the incident light $L_d$ are measured when light is received at predetermined displacement angles $\alpha_1, \alpha_2, \ldots$ outside the incident plane A.

Figure 3:
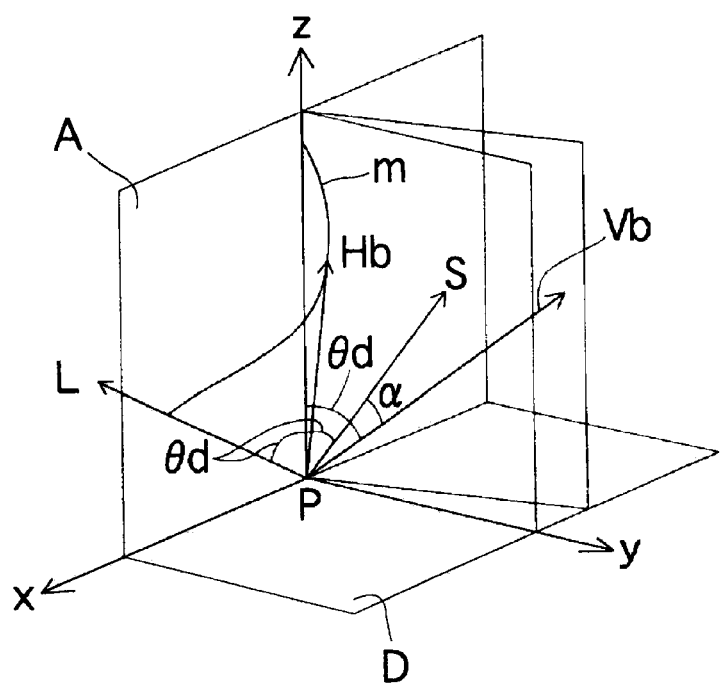
FIG. 3 is a diagram explaining the state where a second reflectance $R(α_b)$ of a second reflected light $V_b$ on a conic plane having an apex as an incident point P, and making an incident angle $θ_d$ with a z axis as a normal line of a plane D under measurement at the incident point P is measured in the second reflectance measuring step in Embodiment 1.

In the second reflectance measuring step of the present embodiment, as shown in FIG. 3, the second reflectances $R(\alpha_{b1}), R(\alpha_{b2}), \ldots$ of the second reflected light $V_{b1}, V_{b2}, \ldots$ on a conic plane of which an apex is the incident point P, and a z axis as a rotation axis acting as a normal line of the plane under measurement (xy plane) D at the incident point P, and a generatrices make a similar angle to the incident angle $\theta_d$, are measured. Namely, in the second reflectance measuring step, the second reflectances $R(\alpha_{b1}), R(\alpha_{b2}), \ldots$ of the second reflected lights $V_{b1}, V_{b2}, \ldots$ located on the conic plane making an angle $\theta_d$ with the z axis are measured.

In this case, as shown in FIG. 3, where the azimuth angle of the second reflected light $V_b$ located on the conic plane making an angle $\theta_d$ with the z axis is taken as Ø, the second reflected lights $V_b$ is expressed by:

$$V_b = (\sin\theta_d \cos\text{\O}, \sin\theta_d \sin\text{\O}, \cos\theta_d).$$

In the present embodiment, as shown in Table 2, $(2\theta_d-1)°$ is selected other than the representative five displacement angles of 10°, 18°, 28°, 40° and 90° as the measurement displacement angles $\alpha_1, \alpha_2, \ldots$ for measuring the second reflectances $R(\alpha_{b1}), R(\alpha_{b2}), \ldots$ in the second reflectance measuring step. And, the measurement displacement angle that can be measured according to the magnitude of the incident angle $\theta_d$ is selected among them.

Namely, when the incident angle $\theta_d$ ranges from 46 to 80° ($\theta_d=46°, 47°, \ldots, 80°$), all of the representative five displacement angles of 10°, 18°, 28°, 40° and 90° are selected as the measurement displacement angles $\alpha_1, \alpha_2, \ldots$.

And when the incident angle $\theta_d$ ranges from 30 to 45° ($\theta_d$=30°, 31°, ..., 45°), four points of 10°, 18°, 28° and 40° among the representative five displacement angles are selected as the measurement displacement angles $\alpha_1$, $\alpha_2$, ....

In this case, when the incident angle $\theta_d$ ranges from 30 to 45°, the reflected light at the displacement angle $\alpha$ of 90° as the representative five displacement angles is not located on the conic plane making an angle $\theta_d$ with the z axis. Therefore, when the incident angle $\theta_d$ ranges from 30 to 44°, the reflectance of the reflected light at the displacement angle $\alpha$ of 90° as the representative five displacement angles is not measured in the second reflectance measuring step. Upon obtaining the second locus m in the second locus determining step, the reflectance of the reflected light at the displacement angle $\alpha$ of $2\theta_d$°, which has been obtained in the first locus determining step, is used for calculation, in place of the reflectance of the reflected light at the displacement angle $\alpha$ of 90° as the representative five displacement angles.

And, when the incident angle $\theta_d$ is 45°, the reflectance of the reflected light at the displacement angle $\alpha$ of 90° ($=2\theta_d$°) as the representative five displacement angles was not actually measured in the second reflectance measuring step. And upon obtaining the second locus m in the second locus determining step, the reflectance of the reflected light at the displacement angle $\alpha$ of $2\theta_d$°, which has been obtained in the first locus determining step, is used for calculation, in place of the reflectance of the reflected light at the displacement angle $\alpha$ of 90° as the representative five displacement angles.

And, when the incident angle $\theta_d$ ranges from 1 to 29° ($\theta_d$=1°, 2°, ... 29°), 1°, 2°, ... $(2\theta_d-1)$° are selected as the measurement displacement angles $\alpha_1, \alpha_2, \ldots$. Namely, when the incident angle $\theta_d$ ranges from 1 to 29°, the reflectance at each angle of 1 through $(2\theta_d-1)$° is measured.

When the incident angle $\theta_d$ is 1°, for example, 1° is selected as the measurement displacement angle $\alpha_1$, when the incident angle $\theta_d$ is 2°, 1°, 2° and 3° are selected as the measurement displacement angles $\alpha_1, \alpha_2, \ldots$, when the incident angle $\theta_d$ is 3°, 1°, 2°, ... and 8° are selected as the measurement displacement angles $\alpha_1, \alpha_2, \ldots$, and when the incident angle $\theta_d$ is 29°, 1°, 2° ... and 57° are selected as the measurement displacement angles $\alpha_1, \alpha_2, \ldots$.

In this case, when the incident angle $\theta_d$ ranges from 1 to 29°, the reflectance of the reflected light at the displacement angle of $2\theta_d$° has been measured in the above-described first reflectance measuring step or calculated in the above-described first locus determining step so as not to be measured in the second reflectance measuring step.

And when the incident angle $\theta_d$ ranges from 81 to 90° ($\theta_d$=81°, 82°, 90°), incident light $L_d$ enters the above-described measurement impossible range, so that the reflectance of the second reflected light $V_a$ cannot be measured. Therefore, in the present embodiment, with respect to the incident light $L_d$ of which the incident angle $\theta_d$ ranges from 81 to 90°, the second reflected light $V_b$ thereof is not measured, but the calculation is performed using the reflectance of the second reflected light $V_b$ of the incident light $L_d$ of which the incident angle $\theta_d$ is 80°.

With respect to the measurement points of which the displacement angle $\alpha$ becomes negative, the reflectances thereof are not measured by virtue of the reciprocity in reflectance.

Therefore, the total of the measurement points at which the second reflectance $R(\alpha_b)$ is measured in the second reflectance measuring step in the present embodiment is obtained from the following equation (18) and becomes 1080 (points).

$$5 \times 35 + 4 \times 16 + \sum_{\theta d=1}^{29}(2\theta d - 1) = 1080 \quad (18)$$

TABLE 2

Second reflectance measuring step (outside incident plane A)

| Incident angle $\theta_d$ (°) | Number of measurement displacement angles | Angle (°) of measurement displacement angles |
|---|---|---|
| 81~90 | — | — |
| 46~80 | 5 | 10, 18, 28, 40, 90 |
| 30-45 | 4 | 10, 18, 28, 40 |
| 1~29 | $2\theta_d - 1$ | 1, 2, ..., $2\theta_d - 1$ |

<Second Locus Determining Step>

In the second locus determining step, a second locus m of termini of second bisection vectors $H_{b1}, H_{b2}, \ldots$, as a curve displacing three-dimensionally outside the incident plane A, is obtained from the measurement results of the second reflectances $R(\alpha_{b1}), R(\alpha_{b2}), \ldots$ obtained in the second reflectance measuring step.

The second bisection vectors $H_{b1}, H_{b2}, \ldots$ are bisection vectors between the second reflected lights $V_{b1}, V_{b2}, \ldots$ outside the incident plane A and on the conic plane making an angle $\theta_d$ with the z axis, and the above-described incident light $L_d$. And in the second bisection vectors $H_{b1}, H_{b2}, \ldots$, the magnitude of each of the second reflectances $R(\alpha_{b1})$, $R(\alpha_{b2}), \ldots$ is defined as the length of each of the second bisection vectors $H_{b1}, H_{b2}, \ldots$, that is $|H_{b1}|=|R(\alpha_{b1})|$, $|H_{b2}|=|R(\alpha_{b2})|, \ldots$.

Therefore, the second locus m of the termini of the second bisection vectors $H_{b1}, H_{b2}, \ldots$ becomes a curve displacing three-dimensionally outside the incident plane A. And, this second locus m approximately shows the reflection distribution of the second reflected lights $V_{b1}, V_{b2}, \ldots$ at each incident angle $\theta_d$.

In this case, one end of the second locus m becomes a point located on the z axis (terminus of the second bisection vector $H_b$ at the displacement angle $\alpha$ of 0°). And, the other end of the second locus m becomes a point located on the incident light vector L (terminus of the second bisection vector $H_a$ at the displacement angle $\alpha$ of $2\theta_d$°).

Upon obtaining the second locus m, the reflectance at the displacement angle other than the measurement points (measurement displacement angles) at which the reflectances have been measured in the second reflectance measuring step can be interpolated, similarly to the above-described first locus determining step.

<Two Intersections Coordinate Determining Step>

As described above, by considering the distribution of microfacets with the bisection vector of the incident light which has been made incident on the plane under measurement coated with the color shifted painting color, and the reflected light thereof, the distribution of the microfacets in the color shifted painting color can be approximated with one part of an ellipsoid of which a center is the incident point P. Therefore, it has become clear that upon taking note of one part of this ellipsoid of which the center is the incident point P, more specifically, one part of an ellipse (an ellipse of which a center is on the z axis as a normal line at an incident point P of the plane under measurement), which is taken along a plane parallel to the plane under measurement (one plane $z=z_1$ vertical to the z axis), the reflection distribution of the color shifted painting color can be approximately modeled with a numerical equation expressing that ellipse.

Figure 4:
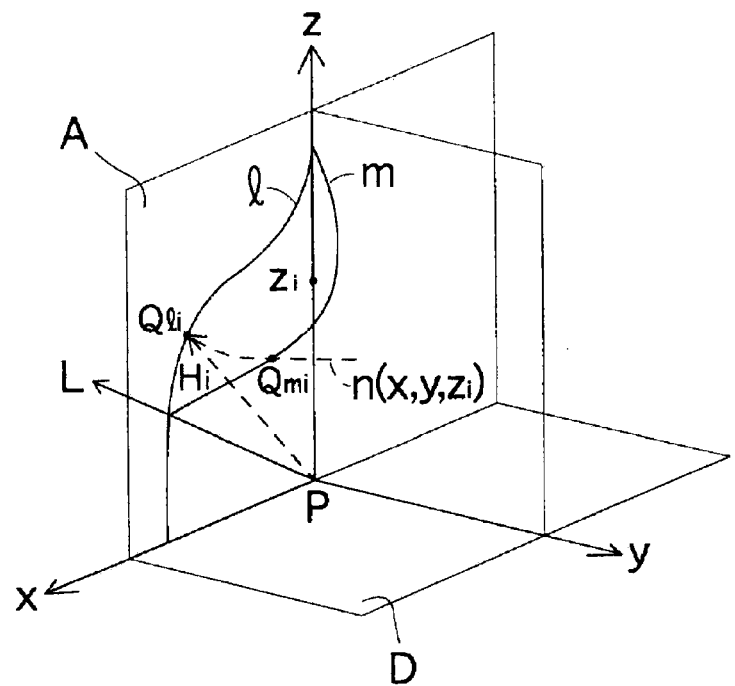
FIG. 4 is a diagram explaining the state where intersections of a first locus l obtained in the first locus determining step, a second locus m obtained in the second locus determining step and a plane $z=z_i$ are determined in the two intersections coordinate determining step in Embodiment 1.

Under the above circumstances, in the two intersections coordinate determining step, as shown in FIG. 4, the plane $z=z_i$ vertical to the z axis in the above-described rectangular coordinate P-xyz is assumed. And an intersection $Q_{li}$ ($x_{li}$, 0, $z_i$) of the plane $z=z_i$ and the above-described first locus l obtained in the above-described first locus determining step is obtained. In addition, an intersection $Q_{mi}$ ($x_{mi}$, $y_{mi}$, $z_i$) of this plane $z=z_i$ and the above-described second locus m obtained in the above-described second locus determining step is obtained.

The intersection $Q_{li}$ ($x_{li}$, 0, $z_i$) thus obtained is a terminus of the first bisection vector $H_a$ on this plane $z=z_i$. And the intersection $Q_{mi}$ ($x_{mi}$, $y_{mi}$, $z_i$) is a terminus of the second bisection vector $H_b$ on this plane $z=z_i$.

<Model Equation Determining Step>

And, in the model equation determining step, as shown in FIG. 4, an approximation model equation (19) in which a locus n (x, y, $z_i$) of the terminus of the bisection vector $H_i$ on the plane $z=z_i$ is modeled approximately with an equation showing an ellipse is obtained from the intersections $Q_{li}$ and $Q_{mi}$ which have been obtained in the two intersections coordinate determining step.

$$(x/a)^2+(y/b)^2=1, z=z_i \qquad (19)$$

This approximation model equation (19) can be obtained from the $Q_{li}$ ($x_{li}$, 0, $z_i$) and the $Q_{mi}$ ($x_{mi}$, $y_{mi}$, $z_i$) using a solution of a simultaneous equation with two unknowns, which is obtained by substituting known two points, for example. In this case, in the approximate model equation (19), a is an x coordinate of a locus n within the incident plane A, and $a=x_{li}$. And, in the approximate model equation (19), b is a y coordinate of the locus n within a plane vertical to the incident plane A.

<Overall Locus Determining Step>

Furthermore, in the overall locus determining step, an overall locus n' (x, y, z) of the overall termini of bisection vectors H' between reflected lights V' other than the first reflected light $V_a$ and the second reflected light $V_b$, and the incident light $L_d$ is approximately obtained under the condition of $z_i=0\sim\infty$.

And, in the method for estimating a reflectance of the present embodiment, the first reflectance measuring step, the first locus determining step, the second reflectance measuring step, the second locus determining step, the two intersections coordinate determining step, the model equation determining step and the overall locus determining step were repeated for each incident light $L_d=L_1, L_2, \ldots, L_{91}$ at a plurality of incident angles $\theta_d=\theta_1, \theta_2, \ldots =0°, 1°, \ldots 90°$ within the range of 0 to 90°. In this case, with respect to the incident light $L_d$ at the incident angle $\theta_d$ of 81 to 90°, as described above, the incident light $L_d$ enters the measurement impossible range so that the reflectance is not measured.

As a result, with the method for estimating a reflectance in the present embodiment, the three-dimensional distribution of reflected lights can be obtained so that the reflectance at not only the displacement angle α inside the incident plane A but also the displacement angle α in three dimensions inclusive of the outside of the incident plane A can be estimated.

In addition, with the method for estimating a reflectance in the present embodiment, the total of the measurement points of the reflectance is 405+1080=1485 (points). This total of the measurement points (1485 points) corresponds to about 3% of the total measurement points 48139 (=23×91×23) points in the above-described all points measuring method. Therefore, in accordance with the method for estimating a reflectance of the present embodiment, the measurement points can be reduced by about 97%, as compared with the above-described all points measuring method.

Furthermore, in the present embodiment, in the above-described second reflectance measuring step, the second reflected light $V_b$ is taken on the conic plane making an incident angle $\theta_d$ with the z axis so that the measurement method becomes simple, and consequently, upon measuring the reflectance R($\alpha_b$) of the second reflected light $V_b$ outside the incident plane A, mistakes such as measurement leaks, etc. can be reduced Embodiment 2

In the method for estimating a reflectance of the present embodiment, the second reflectance measuring step in the method for estimating a reflectance of Embodiment 1 is changed.

Where the second reflected light $V_b$ is taken on the conic plane making an incident angle $\theta_d$ with the z axis, similarly to the second reflectance measuring step of Embodiment 1, one end of the second locus m coincides with one end of the first locus l at one point on the z axis when the displacement angle α is 0°. And, when the displacement angle α is $2\theta_d$, the other end of the second locus m coincides with one point of the first locus l at one point on the incident light vector L. This means that when the displacement angle α is 0° and when the displacement angle α is $2\theta_d°$, no ellipse can be formed. And when the displacement angle α is 0° or in the vicinity of $2\theta_d°$, the two intersections $Q_{li}$ and $Q_{mi}$ adapted to form the ellipse approach to each other, and consequently, the precision of the ellipse obtained from these two intersections $Q_{li}$ and $Q_{mi}$ is lowered.

Figure 5:
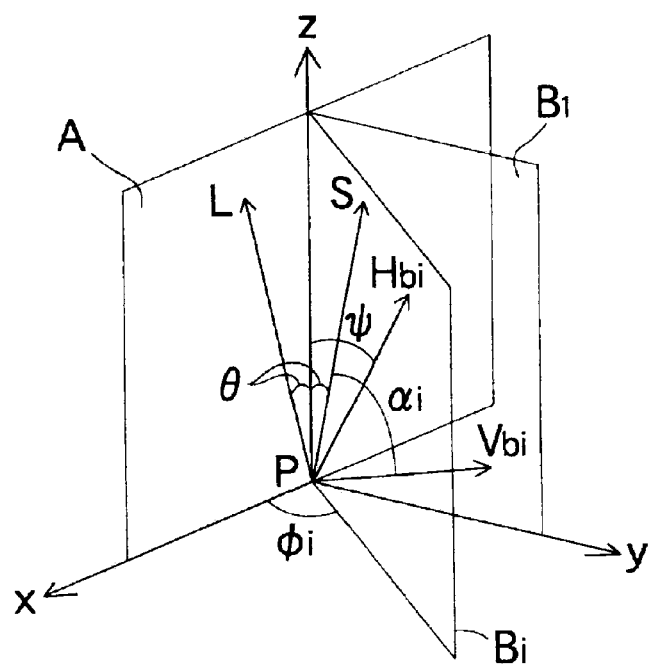
FIG. 5 is a diagram explaining a second bisection vector $H_{bi}$ between an incident light L and a second reflected light $V_{bi}$, which exists inside a plane $B_i$ making an azimuth angle $Ø_i$ with an xz plane as an incident plane A and including a z axis as a normal line of a plane D under measurement at an incident point P in the second reflectance measuring step in Embodiment 2.

In this case, as shown in FIG. 5, a plane $B_i$ making an azimuth angle $\emptyset_i$ ($\emptyset_1=90°, \emptyset_2=89° \emptyset_3=88°, \ldots$) with the xz plane as the incident plane A and including a z axis as a normal line of the plane (xy plane) D under measurement at the incident point P (a plane $B_1$ at an azimuth angle $\emptyset_1$ of 90°, a plane $B_2$ at an azimuth angle $\emptyset_2$ of 89°, a plane $B_3$ at an azimuth angle $\emptyset_3$ of 88°, ...) is assumed.

From the viewpoint of separating the first locus l and the second locus m as far as possible, thereby improving the reliability of the equation showing the above-described ellipse, the locus displacing two-dimensionally inside the plane $B_1$ at the azimuth angle $\emptyset_1$ of 90° is the best as the second locus m, and it is desirable that it is closer to the locus displacing two-dimensionally inside the plane $B_1$.

And, as shown in FIG. 5, where a second reflected light $V_{bi}$ is considered such that a second bisection vector $H_{bi}$ between an incident light L and the second reflected light $V_{bi}$ is located inside the plane $B_i$ at the azimuth angle $\emptyset_i$, an angle between this second bisection vector $H_{bi}$ and the z axis is taken as ψ, and an angle between the regularly reflected light S and the second reflected light $V_{bi}$ is taken as the displacement angle $\alpha_i$, in order to locate the second locus m inside the plane $B_1$, the second bisection vectors $H_{bi}$ at all displacement angles $\alpha_i$, must exist inside the plane $B_1$.

However, as will be explained as follows, as the azimuth angle $\emptyset_i$ of the plane $B_i$ decreases from 90° with the incident angle θ contact, the range in which the second bisection vectors $H_{bi}$ can move inside the plane $B_i$ enlarges. Namely, inside the plane $B_1$ at the azimuth angle $\emptyset_1$ of 90°, the range in which the second bisection vectors $H_{bi}$ can move becomes minimum, as compared with other planes $B_2, B_3, \ldots$.

First, where the second bisection vector $H_{bi}$ inside the plane $B_1$ is expressed by the following equation (20), the incident light L is expressed by the following equation (21) so that the second reflected light $V_{bi}$ is expressed by the following equation (22).

$$H_{bi} = (\sin\psi\cos\varnothing_i, \sin\psi\sin\varnothing_i, \cos\psi) \quad (20)$$

$$L = (\sin\theta, 0, \cos\theta) \quad (21)$$

$$\begin{aligned}V_{bi} &= 2(L \cdot H_{bi})H_{bi} - L \\ &= 2(\sin\theta\sin\psi\cos\varnothing_i + \cos\theta\cos\psi) \cdot \\ &\quad (\sin\psi\cos\varnothing_i, \sin\psi\sin\varnothing_i, \cos\psi) - (\sin\theta, 0, \cos\theta)\end{aligned} \quad (22)$$

Namely, where the x coordinate, y coordinate and z coordinate of the second reflected light $V_{bi}$ are taken as $V_x, V_y, V_z$, respectively, $V_x, V_y, V_z$ are expressed by the following equation (23), equation (24) and equation (25), respectively.

$$V_x = 2(\sin\theta\sin\psi\cos\varnothing_i + \cos\theta\cos\psi) \cdot (\sin\psi\cos\varnothing_i) - \sin\theta \quad (23)$$

$$V_y = 2(\sin\theta\sin\psi\cos\varnothing_i + \cos\theta\cos\psi) \cdot (\sin\psi\sin\varnothing_i) \quad (24)$$

$$V_z = 2(\sin\theta\sin\psi\cos\varnothing_i + \cos\theta\cos\psi) \cdot (\cos\psi) - \cos\theta \quad (25)$$

Therefore, the z coordinate $V_z$ of the second reflected light $V_{bi}$ is expressed by the following equation (26).

$$\begin{aligned}V_Z &= \sin\theta\cos\phi_1\sin 2\psi + \cos\theta\cos 2\psi \\ &= \sqrt{\sin^2\theta\cos^2\phi_1 + \cos^2\theta} \cdot \sin(2\psi + \xi)\end{aligned} \quad (26)$$

In this equation, $\xi$ satisfies the following equation (27).

$$\tan\xi = \cos\theta/(\sin\theta\cos\varnothing_i) \quad (27)$$

And, an angle $\eta$ between the second reflected light $V_{bi}$ and the xy plane is expressed by the following equation (28).

$$\eta = \tan^{-1}\left(\frac{v_z}{\sqrt{v_x^2 + v_y^2}}\right) \quad (28)$$

The second reflected light $V_{bi}$ cannot enter the above-described measurement impossible range due to the structural limitations of the measuring machine so that the angle $\eta$ between the second reflected light $V_{bi}$ and the xy plane becomes $\eta \geq 10$. And a maximum value of $\psi$, which makes $\eta$ satisfying $\eta \geq 10$ minimum, is expressed by $\psi_{max}$. In this case, when the incident angle $\theta$ is constant, $\psi_{max}$ becomes a function of the azimuth angle $\varnothing_i$, and increases with the decrement of the azimuth angle $\varnothing_i$.

Figure 6:
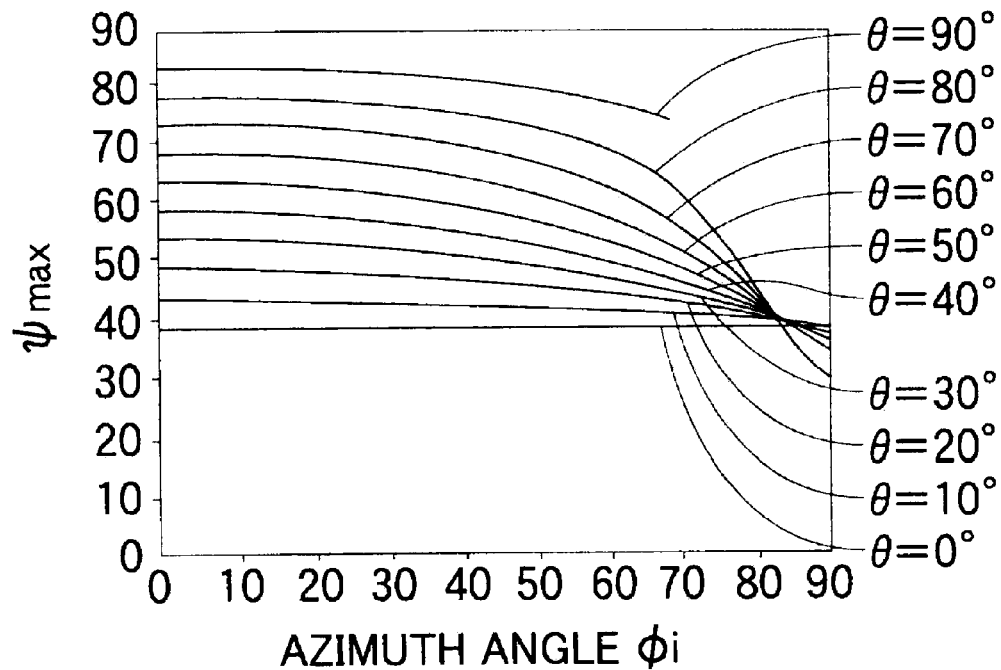
FIG. 6 is a diagram showing the relationship between a maximum value $ϕ_{max}$ making an angle η between the second reflected light $V_{bi}$ and the xy plane minimum and the azimuth angle $Ø_i$ of the plane $B_i$, and explaining that as the azimuth angle $Ø_i$ of the plane $B_i$ decreases from 90°, the range in which the second bisection vector $H_{bi}$ can move inside the plane $B_i$ enlarges in the second reflectance measuring step in Embodiment 2.

When the incident angle $\theta$ is constant, the relationship between the $\psi_{max}$ and the azimuth angle $\varnothing_i$ is shown in FIG. 6, using the above-described equation (28). FIG. 6 shows that when the incident angle $\theta$ is constant, the second bisection vector $H_{bi}$ can move in an enlarged range of the plane $B_i$ as the azimuth angle $\varnothing_i$ thereof decreases from 90°.

Figure 7:
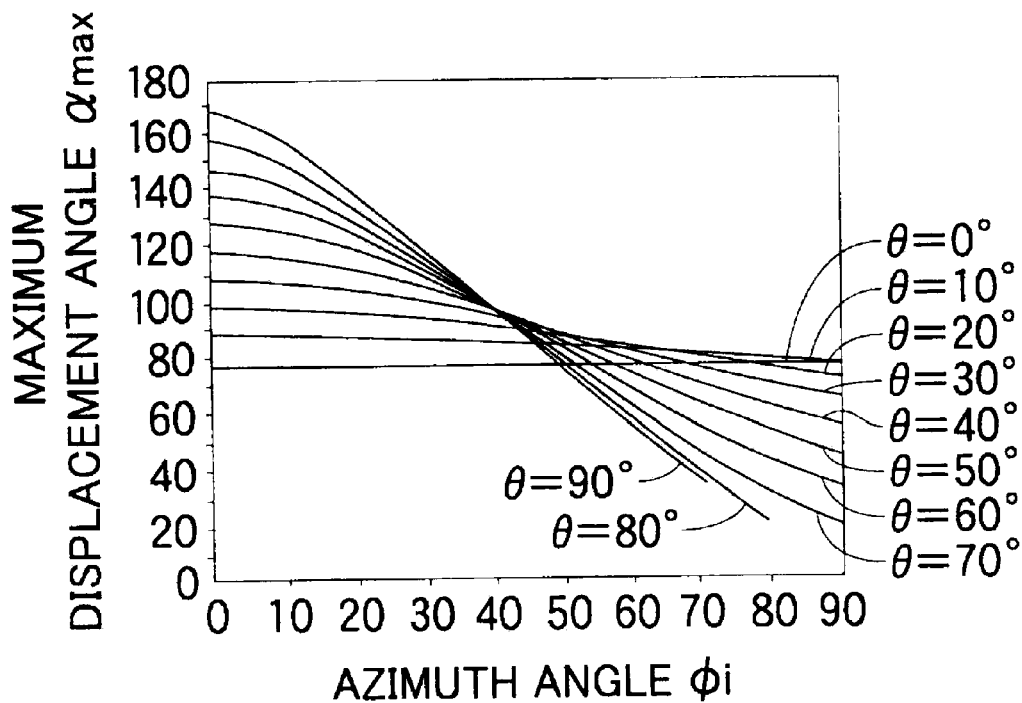
FIG. 7 is a diagram showing the relationship between the azimuth angle $Ø_i$ of the plane $B_i$ and a maximum value $α_{max}$ of a displacement angle $α_i$ of the second reflected light $V_{bi}$ of which the second bisection vector $H_{bi}$ exists inside the plane $B_i$ at the azimuth angle $Ø_i$, and explaining that as the azimuth angle $Ø_i$ decreases, the maximum displacement angle $α_{max}$ increases in the second reflectance measuring step in Embodiment 2.

And, as shown in FIG. 7, when the incident angle $\theta$ is constant, the azimuth angle $\varnothing_i$ of the plane $B_i$, and the maximum displacement angle $\alpha_{max}$ of the displacement angle $\alpha_i$ of the second reflected light $V_{bi}$ of which the second bisection vector $H_{bi}$ is located inside the plane $B_i$ of the azimuth angle $\varnothing_i$ have such a relationship that as the azimuth angle $\varnothing_i$ decreases, the maximum displacement angle $\alpha_{max}$ increases. In this case, the maximum displacement angle $\alpha_{max}$ means the maximum displacement angle among the displacement angles $\alpha_i$ between the second reflected light $V_{bi}$ of which the second bisection vector $H_{bi}$ is located inside the plane $B_i$, and the above-described regularly reflected light S where the incident light L and the second reflected light $V_{bi}$ do not enter the above-described measurement impossible range.

Therefore, as is apparent from FIG. 7, where the incident angle $\theta$ is 60°, for example, the maximum displacement angle $\alpha_{max}$ is about 32 to 33° in the plane $B_i$ of the azimuth angle $\varnothing_i$ is 90° so that only 10°, 18° and 28° can be selected among the representative five displacement angles, and the second bisection vectors $H_{bi}$ of the second reflected lights $V_{bi}$ at these three displacement angles are located inside the plane $B_1$. And in order to select 40° of the five displacement angles, the azimuth angle $\varnothing_i$ must be about 80° or more such that the maximum displacement angle $\alpha_{max}$ becomes about 40° or more, and in order to select 90° of the above-described five displacement angles, the azimuth angle $\varnothing_i$ must be about 45° or more such that the maximum displacement angle $\alpha_{max}$ becomes about 90° or more.

Therefore, the second locus m displacing two-dimensionally only inside the plane $B_1$ of which the azimuth angle is 90° cannot be obtained.

Under the above circumstances, in the second reflectance measuring step of the present embodiment, in order to make the second locus m closer to that displacing two-dimensionally only inside the plane $B_1$ of which the azimuth angle is 90°, the following steps are performed.

First, in a first step, the above-described second reflectances $R(\alpha_{b1}), R(\alpha_{b2}), \ldots$ of the second reflected lights $V_{b1}, V_{b2}, \ldots$ of which the second bisection vectors $H_{b1}, H_{b2}, \ldots$ are located inside the plane $B_1$ are measured in such a range that the displacement angles can be selected starting from a smaller angle out of the representative five displacement angles as many as possible.

And, when in a (f−1) step just therebefore, at least one part of the representative five displacement angles cannot be selected such that the second bisection vectors are located inside the plane $B_{f−1}$, and consequently, at least one part of the second reflectances $R(\alpha_{b1}), R(\alpha_{b2}), \ldots$ was not obtained, a fth step of measuring the second reflectances $R(\alpha_{b1}), R(\alpha_{b2}), \ldots$ of the second reflected lights $V_{b1}, V_{b2}, \ldots$ of which the second bisection vectors $H_{b1}, H_{b2}, \ldots$ are located inside not the plane $B_{f−1}$ but the plane $B_f$ in such a range that the representative five displacement angles can be selected starting from a smaller angle out of at least one part of the representative five displacement angles, which have not been selected in the (f−1) step, as many as possible, is repeatedly performed as a second step, a third step, . . . .

Namely, when, in the first step, at least one part of the representative five displacement angles cannot be selected such that the second bisection vectors are located inside the plane $B_1$, and consequently, at least one part of the second reflectances $R(\alpha_{b1}), R(\alpha_{b2}), \ldots$ was not obtained, the second step of measuring the second reflectances $R(\alpha_{b1}), R(\alpha_{b2}), \ldots$ of the second reflected lights $V_{b1}, V_{b2}, \ldots$ of which the second bisection vectors $H_{b1}, H_{b2}, \ldots$ are located inside not the plane $B_1$ but the plane $B_2$ in such a range that displacement angles can be selected starting from a smaller angle out of at least one part of the representative five displacement angles, which have not been selected in the first step, as many as possible, is performed.

And, when, in the second step, at least one part of the representative five displacement angles cannot be selected such that the second bisection vectors are located inside the plane $B_2$, and consequently, at least one part of the above-described second reflectances $R(\alpha_{b1}), R(\alpha_{b2}), \ldots$ was not obtained, the third step of measuring the second reflectances $R(\alpha_{b1})$, $R(\alpha_{b2})$, ... of the second reflected lights $V_{b1}$, $V_{b2}$, ... of which the second bisection vectors $H_{b1}$, $H_{b2}$, ... are located inside not the plane $B_2$ but the plane $B_3$ in such a range that displacement angles can be selected starting from a smaller angle out of at least one part of the representative five displacement angles, which have not been selected in the second step, as many as possible, is performed.

In addition, when, in the third step, at least one part of the representative five displacement angles cannot be selected such that the second bisection vectors are located inside the plane $B_3$, and consequently, at least one of the second reflectances $R(\alpha_{b1})$, $R(\alpha_{b2})$, ... was not obtained, the fourth step is performed, similarly to the third step.

By performing the first step, the second step, the third step, ... in this order, the second reflectances $R(\alpha_{b1})$, $R(\alpha_{b2})$, ... of the second reflected lights $V_{b1}$, $V_{b2}$, ... of which the second bisection vectors $H_{b1}$, $H_{b2}$, ... at the above-described representative five displacement angles are located inside one of the planes $B_1$, $B_2$, $B_3$, ... are measured.

In this case, the measurement points (measurement displacement angles) in the above-described first step, second step, third step, ... can be determined in the following method.

The regularly reflected light S of a light source L against the plane under measurement D is expressed by the following equation (29), and consequently, by expressing the displacement angle between the regularly reflected light S and the second reflected light $V_{b1}$ is by $\alpha_i$, $\psi$ is expressed by the following equation (31), using the following equation (30).

$$S = (\sin\theta, 0, \cos\theta) \quad (29)$$

$$S \cdot V_{bi} = 1 \cdot 1 \cdot \cos\alpha_i \quad (30)$$
$$= 2(\cos^2\theta\cos^2\psi - \sin^2\theta\sin^2\psi\cos^2\varnothing_1) - \cos 2\theta$$

$$\sin\psi = \sqrt{\frac{\cos\phi_1 - 1}{2\{\sin^2\theta(1-\cos^2\phi_1) - 1\}}} \quad (31)$$

Where the displacement angle $\alpha_i$ between the regularly reflected light S and the second reflected light $V_{bi}$ and the azimuth angle $\varnothing_i$ are determined, $\psi$ is determined from the equation (31).

<First Step>

First, the selectable displacement angles $\alpha_i$ such as 0°, 1°, 2°, ..., are examined when the azimuth angle $\varnothing_i$ is 90° ($\varnothing_i$=90°). $\psi$ at $\alpha_i$=0°, 1°, 2°, ... is obtained using the above-described equation (31) while taking care of the movable range of $\psi$ relative to the incident angle $\theta$, as shown in FIG. 6. And the maximum displacement angle $\alpha_{max}$ (see FIG. 7) at the azimuth angle $\varnothing_i$ of 90° is expressed by $\alpha_{90}$. Namely, at the azimuth angle $\varnothing_i$=90°, the displacement angle $\alpha_i$ is taken as $\alpha_i$=0°, 1°, 2°, ..., $\alpha_{90}$.

And, it is examined whether the obtained displacement angle $\alpha_i$ agrees to 10°, 18°, 28°, 40° or 90° as the above-described representative five displacement angles from a smaller angle thereof. Where the displacement angle $\alpha_i$ agrees to one of the representative five displacement angles or is approximately equal thereto at the azimuth angle $\varnothing_i$ of 90°, a set of the azimuth angle $\varnothing_i$ of 90°, $\psi$, $\alpha_{90}$, and the representative five displacement angles 10°, 18°, ... to which the angle $\alpha_i$ agrees or is approximately equal at that time ($\varnothing_i$=90°, $\psi$, $\alpha_{90}$, 10°, 18°, ... ) is memorized. This memorized set of the representative five displacement angles 10°, 18°, ... becomes measurement points (measurement displacement angles) to be measured in the first step.

<Second Step>

Next, the selectable displacement angles $\alpha_i$ such as a $\alpha_{90}$+1, $\alpha_{90}$+2, $\alpha_{90}$+3, ..., are examined in the case of the azimuth angle $\varnothing_i$ being decreased by 1° ($\varnothing_2$=89°), and $\psi$ corresponding to respective $\alpha_i$ is obtained using the above-described equation (31).

And, the above-described maximum displacement angle $\alpha_{max}$ at the azimuth angle $\varnothing_2$ of 89° is expressed by $\alpha_{89}$. Namely, in the case of $\varnothing_2$ being 89°, the displacement angles $\alpha_i$ is determined to $\alpha_i$=$\alpha_{90}$+1, $\alpha_{90}$+2, $\alpha_{90}$+3, ... $\alpha_{89}$. And it is examined whether there are representative five displacement angles different from or greater than the measurement displacement angle at $\varnothing_1$ of 90° or not. If there are such representative five displacement angles, a set of the azimuth angle $\varnothing_2$ of 89°, $\psi$, $\alpha_{89}$, and the representative five displacement angles ..., 40°, 90° to which the angle $\alpha_i$ agrees or is approximately equal at that time ($\varnothing_2$=89°, $\psi$, $\alpha_{89}$, ... 40°, 90°) is memorized, similarly. In this case, if there is no such representative five displacement angles, no operation is performed. This memorized set of the representative five displacement angles ..., 40°, 90° becomes measurement points (measurement displacement angles) to be measured in the second step.

<Third Step, Fourth Step, ... >

In addition, by decreasing the azimuth angle $\varnothing_i$ by 1° to $\varnothing_3$=88°, the measurement points to be measured in the third step are obtained, similarly, and by continuously decreasing the azimuth angle $\varnothing_i$ by 1° ($\varnothing_i$=87°, 86°, ..., 0°), similar procedure is performed.

In this manner, these steps are continued until the displacement angle $\alpha_i$ agrees or becomes approximately equal to the representative five displacement angles of 10°, 18°, 28°, 40°, 90° for any azimuth angle $\varnothing_i$ ($\varnothing_i$=0 to 90°).

Where the representative five angle of 90° cannot be selected as the measurement displacement angle for any azimuth angle $\varnothing_i$ or any $\psi$, the azimuth angle $\varnothing_i$ is varied, and when $\alpha_i$ becomes 70°, for example, $\alpha_i$=70° can be taken as the measurement displacement angle in place of $\alpha_i$=90°.

These operations are related only to the geometric conditions so that when the measuring machine is determined and the measurement impossible range is determined, all points to be measured can be obtained prior to measurement. Therefore, the representative five displacement angles can be obtained against all incident angle $\theta$ ($\theta$=0 to 90°) while varying the azimuth angle $\varnothing_i$.

Figure 8:
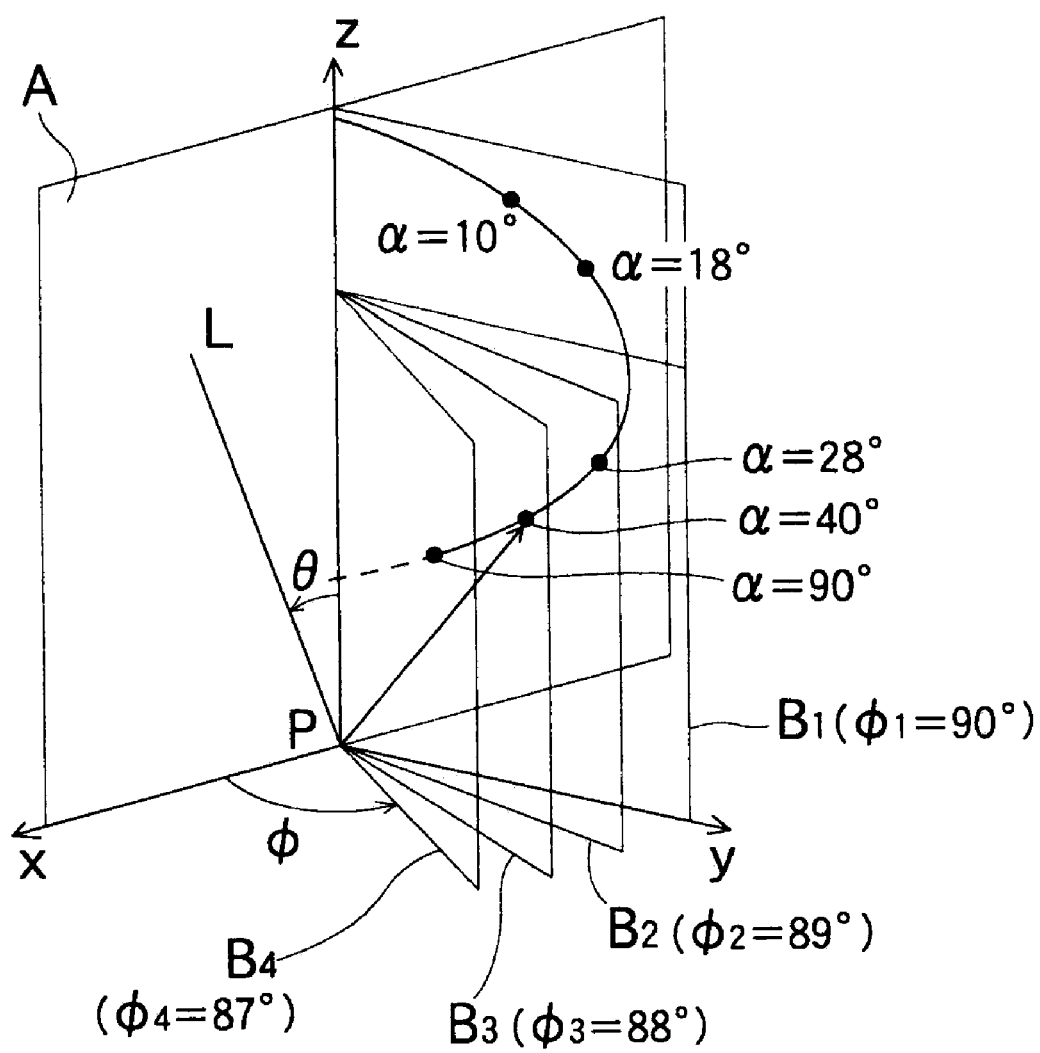
FIG. 8 is a diagram explaining one example of a second locus m as a curve displacing three-dimensionally outside the incident plane A, which is obtained in the second locus determining step in Embodiment 2.

In this manner, the azimuth angle $\varnothing_i$ and $\psi$ against respective $\alpha_i$=0°, 1°, 2°, ..., 90°, which have been obtained by varying the azimuth angle $\varnothing_i$ and $\psi$, are determined. Consequently, the directions of the second bisection vectors $H_{b1}$, $H_{b2}$, ... are determined. Therefore, the second reflectance $R(\alpha_b)$ at all of the displacement angles $\alpha_i$ ($\alpha_i$=0°, 1°, 2°, ..., 90°) can be obtained from the second reflectances $R(\alpha_{b1})$, $R(\alpha_{b2})$, $R(\alpha_{b3})$, $R(\alpha_{b4})$, $R(\alpha_{b5})$ at the representative five displacement angles of 10°, 18°, 28°, 40°, 90°, which have been obtained in this second reflectance measuring step, similarly to Embodiment 1. As a result, by taking a point of $|H_b|=|R(\alpha_b)|$ on the second bisection vectors $H_{b1}$, $H_{b2}$, ..., similarly to Embodiment 1, as shown in FIG. 8, for example, a second locus m as a curve displacing three-dimensionally outside the incident plane A, can be obtained.

The second locus m thus obtained in the present embodiment separates from the first locus l inside the incident plane A far away so that the numerical equation of the ellipse showing the distribution of the reflected light can be specified more accurately, whereby the reflectance can be estimated more precisely.

And when the incident angle θ enters the measurement impossible range, namely when θ is 81°, 82°, ..., 90°, the reflectance obtained when θ is 80° is used in order to enhance the efficiency of the calculation, and shorten the measuring time. With this method, the number of the measuring points for measuring the second reflectance $R(\alpha_b)$ in the second reflectance measuring step in the present embodiment becomes 81×5=405 (points).

Therefore, with the reflectance measuring method in the present embodiment, the total of the measuring points of the reflectance in the above-described first reflectance measuring step and the second reflectance measuring step becomes 405+405=810 (points). This total of the measuring points (810) corresponds to about 2% of the number of all measuring points 48139(=23×91×23) with the above-described all points measuring method. Consequently, with the method for estimating a reflectance of the present embodiment, about 98% of the measuring points have been able to be reduced, as compared to the above-described all points measuring method.

EXAMPLE

Example 1

The coated surface of a vehicle, which had been obtained by coating a vehicle body with a color shifted painting color, was measured using a three-dimensional spectrophotometer ([GCMS-4] manufactured by MURAKAMI COLOR RESEARCH LABORATORY) as a measuring machine with a method according to the method for estimating a reflectance, which has been explained in the above-described EMBODIMENT 1.

As a result, the time required for this measurement was about 4 hours.

And, upon storing the measured reflectance in LUT (Look Up Table), and performing calculation with 6CPU (Intel Xeon 3.06 GHz) and a size of a resolution SXGA, the calculating time of a picture image was 12 minutes 24 seconds.

Furthermore, the accuracy of the picture image was evaluated. This was performed by comparing the method of the present example with the above-described conventional five angles method about the picture image and numerical value where the picture image with the above-described all points measuring method is taken as a positive value.

As a result, there was scarcely a difference between the all points measuring method and the method of the present example, the average color difference in area other than the vicinity of a highlight (the displacement angle of 10° or less) was 2.76.

In contrast, there was a large difference between the all points measuring method and the above-described conventional five angles method, and the average color difference in area other than the vicinity of highlights (the displacement angle of 10° or less) was 20.50.

And the picture image of which color was reproduced with the method of the present example was similar to that with the all points measuring method in variation of hue and contrast, and was drastically improved, as compared with that with the above-described conventional five angles method.

Therefore, with the method of the present example, the color shifted painting color that has not been presented with the above-described conventional five angles method can be reproduced with a good color.

The invention claimed is:

1. A method for estimating a reflectance at an arbitrary displacement angle inside an incident plane A and outside the incident plane A, by taking an angle between a regularly reflected light S of an incident light L, which is regularly reflected inside the incident plane A when the incident light L is made incident on an incident point P on a plane under measurement at a predetermined incident angle θ, and a reflected light V of the incident light L, which is reflected and received from the incident point P, as a displacement angle α, the method for estimating a reflectance being characterized in that the method includes a first reflectance measuring step of measuring first reflectances $R(\alpha_{a1})$, $R(\alpha_{a2})$, ... of first reflected lights $V_{a1}$, $V_{a2}$, ... inside the incident plane A, which are obtained by making an incident light $L_d$ incident on the incident point P inside the incident plane A at an incident angle $\theta_d$, and receiving light at predetermined displacement angles $\alpha_1$, $\alpha_2$, ... inside the incident plane A, relative to the incident light $L_d$, a first locus determining step of by taking bisection vectors between said incident light $L_d$ and said first reflected lights $V_{a1}$, $V_{a2}$, ... as first bisection vectors $H_{a1}$, $H_{a2}$ ..., and defining the magnitude of said first reflectance $R(\alpha_a)$ as $|H_a|=|R(\alpha_a)|$, determining a first locus l of termini of said first bisection vectors $H_{a1}$, $H_{a2}$, ... as a curve displacing two-dimensionally inside the incident plane A from the measurement results of said first reflectances $R(\alpha_{a1})$, $R\alpha_{a2})$, ..., a second reflectance measuring step of measuring second reflectances $R(\alpha_{b1})$, $R(\alpha_{b2})$, ... of second reflected lights $V_{b1}$, $V_{b2}$, ... outside the incident plane A, which are obtained by making said incident light $L_d$ incident on the incident point P inside the incident plane A at said incident angle $\theta_d$, and receiving light at predetermined displacement angles $\alpha_1$, $\alpha_2$, ... outside the incident plane A, relative to said incident light $L_d$, a second locus determining step of, by taking bisection vectors between said incident light $L_d$ and said second reflected lights $V_{b1}$, $V_{b2}$, ... as second bisection vectors $H_{b1}$, $H_{b2}$, ... and defining the magnitude of said second reflectance $R(\alpha_b)$ as $|H_b|=|R(\alpha_b)|$, determining a second locus m of termini of said second bisection vectors $H_{b1}$, $H_{b2}$, ... as a curve displacing three-dimensionally outside the incident plane A from the measurement results of said second reflectances $R(\alpha_{b1})$, $R(\alpha_{b2})$, ..., two intersections coordinate determining step of, upon assuming a rectangular coordinate P-xyz existing in a space in which an x axis, a y axis and a z axis cross at right angles and share the incident point P as an origin thereof, and of which an xy plane acts as the plane under measurement and an xz plane inclusive of the incident point P acts as the incident plane A, determining intersections $Q_{li}(x_{li}, 0, z_i)$ and $Q_{mi}(X_{mi}, Y_{mi}, z_i)$ of a plane $z=z_i$ that is vertical to said z axis, and said first locus l and said second locus m, a model equation determining step of approximately modeling a locus n (x, y, $z_i$) of a terminus of a bisection vector $H_i$ on said plane $z=z_i$ from said intersections $Q_{li}$ and $Q_{mi}$ with an equation showing a smooth curve passing said intersections $Q_{li}$ and $Q_{mi}$, thereby determining an approximation model equation, and an overall locus determining step of approximately determining an overall locus n' (x, y, z) of said overall termini of a bisection vector H' between a reflected light V' other than said first reflected light $V_a$ and said second reflected light $V_b$, and said incident light $L_d$, from said approximation model equation under the condition of $z_i$=0~∞, said displacement angles $\alpha_1, \alpha_2, \ldots$ including at least one displacement angle selected from N ($1 \leq N \leq 89$) representative N displacement angles prescribed in a range of 0 through 90°, said first reflectance measuring step, said first locus determining step, said second reflectance measuring step, said second locus determining step, said two intersections coordinate determining step, said model equation determining step and said overall locus determining step being repeated for each incident light $L_d = L_1, L_2, \ldots$ at a plurality of incident angles $\theta_d = \theta_1, \theta_2, \ldots$ within a range of 0 through 90°.

2. A method for estimating a reflectance as claimed in claim 1, wherein said smooth curve passing said intersections $Q_{li}$ and $Q_{mi}$ is an ellipse.

3. A method for estimating a reflectance as claimed in claim 1, wherein in said second reflectance measuring step, said second reflectances $R(\alpha_{b1}), R(\alpha_{b2}), \ldots$ of said second reflected lights $V_{b1}, V_{b2}, \ldots$ existing on a conic plane of which an apex is the incident point P, and a z axis as a rotation axis that is a normal line of the plane under measurement at the incident point P, and a generatrices make a similar angle to said incident angle $\theta_d$, are measured.

4. A method for estimating a reflectance as claimed in claim 1, wherein in said second reflectance measuring step, upon assuming planes $B_1, B_2, B_3, \ldots$ making an azimuth angle of $\varnothing_1 = 90°, \varnothing_2 = (90-e)°, \varnothing_3 = (90-2e)°$, wherein e is an arbitrary positive number, $\ldots$ with said xz plane as the incident plane A, and including said z axis as said normal line of the plane under measurement at the incident point P, a first step of measuring said second reflectances $R(\alpha_{b1}), R(\alpha_{b2}), \ldots$ of said second reflected lights $V_{b1}, V_{b2}, \ldots$ such that said second bisection vectors $H_{b1}, H_{b2}$, exist inside said plane $B_1$ within a range in which said representative N displacement angles are selected as many as possible starting from a smaller angle, is performed, and where in a (f−1) step just therebefore, at least one part of said second reflectances $R(\alpha_{b1}), R(\alpha_{b2}), \ldots$ has not been measured, because at least one part of said representative N displacement angles has not been selected such that said second bisection vectors exist inside a plane $B_{f-1}$, a f step of measuring said second reflectances $R(\alpha_{b1}), R(\alpha_{b2}), \ldots$ of said second reflected lights $V_{b1}, V_{b2}, \ldots$ such that said second bisection vectors $H_{b1}, H_{b2}, \ldots$ exist inside not said plane $B_{f-1}$ but said plane $B_f$ within a range in which at least one part of said representative N displacement angles, which has not been selected in said (f−1) step, is selected as many as possible starting from a smaller angle, is repeatedly performed as a second step, a third step, $\ldots$, whereby said second reflectances $R(\alpha_{b1}), R(\alpha_{b2}), \ldots$ of said second reflected lights $V_{b1}, V_{b2}, \ldots$ of which said second bisection vectors $H_{b1}, H_{b2}, \ldots$ at said representative N displacement angles exist inside each of said plane $B_1, B_2, B_3, \ldots$ are measured.

5. A method for estimating a reflectance as claimed in claim 1, wherein said representative N displacement angles are representative five angles of about 10°, about 18°, about 28°, about 40° and about 90°.

6. A method for estimating a reflectance as claimed in claim 1, wherein said plane under measurement is coated with a color shifted painting color.

* * * * *